(12) United States Patent
During et al.

(10) Patent No.: US 7,655,619 B2
(45) Date of Patent: Feb. 2, 2010

(54) INSULIN-ASSOCIATED PEPTIDES WITH EFFECTS ON CEREBRAL HEALTH

(75) Inventors: Matthew J. During, Philadelphia, PA (US); Colin N. Haile, Katy, TX (US)

(73) Assignee: Thomas Jefferson University, Philadelphia, PA (US)

( * ) Notice: Subject to any disclaimer, the term of this patent is extended or adjusted under 35 U.S.C. 154(b) by 245 days.

(21) Appl. No.: 10/430,545

(22) Filed: May 6, 2003

(65) Prior Publication Data

US 2004/0014660 A1 Jan. 22, 2004

Related U.S. Application Data

(60) Provisional application No. 60/378,318, filed on May 6, 2002.

(51) Int. Cl.
*A61K 38/28* (2006.01)
*A61K 38/12* (2006.01)
(52) U.S. Cl. .............................. 514/3; 514/13; 514/11
(58) Field of Classification Search ....................... None
See application file for complete search history.

(56) References Cited

U.S. PATENT DOCUMENTS

| 4,659,696 | A | * | 4/1987 | Hirai et al. ................ 514/15 |
| 5,725,860 | A | * | 3/1998 | Elliott ..................... 424/240.1 |
| 5,747,445 | A | * | 5/1998 | Backstrom et al. ............. 514/4 |
| 6,313,093 | B1 | | 11/2001 | Frey, II |
| 6,335,361 | B1 | | 1/2002 | Hamilton |
| 6,407,061 | B1 | | 6/2002 | Frey, II |

FOREIGN PATENT DOCUMENTS

| DE | 19826628 C1 | 7/2000 |
| WO | 00/61177 | 10/2000 |

OTHER PUBLICATIONS

Bullesbach EE et al. Functional importance of the A chain loop in relaxin and insulin. J Biol Chem, 1994; 269(18): 13124-13128.*
Diaz Brinton R and Yamazaki RS. Advances and challenges in the prevention and treatment of Alzheimer's disease. Pharm Res, 1998; 15(3): 386-398.*
Fehm HL et al. Manipulating neuropeptidgergic pathways in humans: a novel approach to neuropharmacology? Eur J Pharm, 2000; 405: 43-54.*
Feigin A and Zgaljardic D. Recent advances in Huntington's disease: Implications for experimental therapeutics. Curr Opin Neurol, 2002; 15: 483-489.*
Shao Z et al. Cyclodextrins as nasal absorption promoters of insulin: mechanistic evaluations. Pharm Res, 1992; 9(9): 1157-1163.*
Steece-Collier K et al. Etiology of Parkinson's disease: Genetics and environment revisited. Proc Natl Acad Sci USA, 2002; 99(22): 13972-13974.*
Reger MA et al. Effects of intranasal insulin on cognition in memory-impaired older adults: Modulation by APOE genotype. Neurobiology Aging, 2006; 27:451-458.*
Wan et al. Biochem. 2005, 44:5000-5016.*
Yan et al. Science, 2000, 290(5491):523-527.*
Liu XF et al. J Neurological Sci. 2001, 187:91-97.*
Sasaki N et al. J Biol Chem. 1985, 260(17):9793-9804.*
Brandt, Burkhard et al. "Early Placenta Insulin-Like Growth Factor (pro-EPIL) is Over-Expressed And Secreted By c-erbB-2-Positive Cells With High Invasion Potential," Cancer Research, pp. 1020-1024 (2002).
Claeys, Ilse et al. "Insulin-Related Peptides And Their Conserved Signal Transduction Pathway," Peptides, vol. 23, pp. 807-816 (2002).
Gasparini, Laura et al. "Does Insulin Dysfunction Play A Role In Alzheimer's Disease," Trends in Pharmacological Sciences, vol. 23, No. 6, pp. 288-293 (2002).
Park, Collin R. et al. "Intracerebroventricular Insulin Enhances Memory In A Passive-Avoidance Task," Physiology & Behavior, vol. 68, pp. 509-514 (2000).
Tatar, Marc et al. "The Endocrine Regulation of Aging by Insulin-Like Signals," Science, vol. 299, pp. 1346-1351, (2003).
Zhao, Wei-Qin and Alkon, Daniel L. "Role of Insulin And Insulin Receptor In Learning And Memory," Molecular and Cellular Endocrinology, vol. 177, pp. 125-134 (2001).
Cooper, G.J.S. et al. "Purification and Characterization of a Peptide From Amyloid-Rich Pancreases of Type 2 Diabetic Patients," Proc. Natl. Acad., Sci USA, vol. 84, pp. 8628-8632 (1987).
O'Brien, T.D. "Pathogenesis of Feline Diabetes Mellitus," Molecular and Cellular Endocrinology, vol. 197, pp. 213-219, (2002).
Zhang, Yi et al. "Nasal Absorption Enhancement of Insulin By Sodium Deoxycholate In Combination With Cyclodextrins," Acta Pharmacol Sin, vol. 22, No. 11, pp. 1051-1056 (2001).
Craft et al., "Enhancement of Memory In Alzheimer Disease With Insulin And Somatostatin, But Not Glucose", Arch Gen Psychiatry, vol. 56, pp. 1135-1141.
Kern et al., "Improving Influence Of Insulin On Cognitive Functions In Humans", Neuroendocrinology, vol. 74, pp. 270-280, 2001.
European Search Report dated Jul. 31, 2009 for European Patent Application No. 03 74 7673.6.

* cited by examiner

*Primary Examiner*—Elizabeth C. Kemmerer
*Assistant Examiner*—Kimberly A. Ballard
(74) *Attorney, Agent, or Firm*—Nutter McClennen & Fish LLP; Thomas J. Engellenner

(57) ABSTRACT

The present invention provides compositions and methods for ameliorating neurological, attention, or memory disorders and improving learning and cognition through the delivery of insulin A-chain and analogs thereof to a subject. Insulin A-chain, peptides comprising the 21 amino acid sequence GIVEQ CCASV CSLYQ LENYC N (SEQ ID NO:1), and functional analogs thereof are disclosed to modulate neurological activity when administered to a subject. The methods of the invention can be used to prevent or treat neurological disorders as well as improve memory retention and acquisition. The invention includes pharmaceutical compositions comprising a therapeutically or prophylactically effective amount of insulin A-chain peptide or a functional analogs thereof.

23 Claims, 10 Drawing Sheets

Figure 1 - HUMAN INSULIN

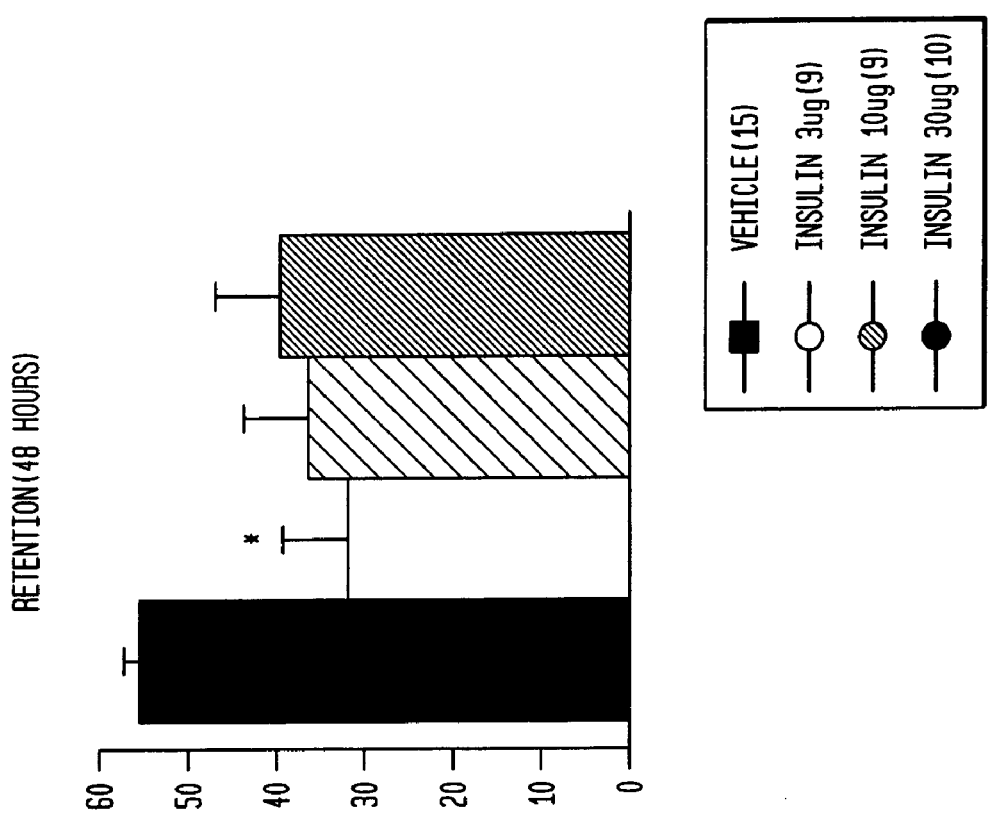
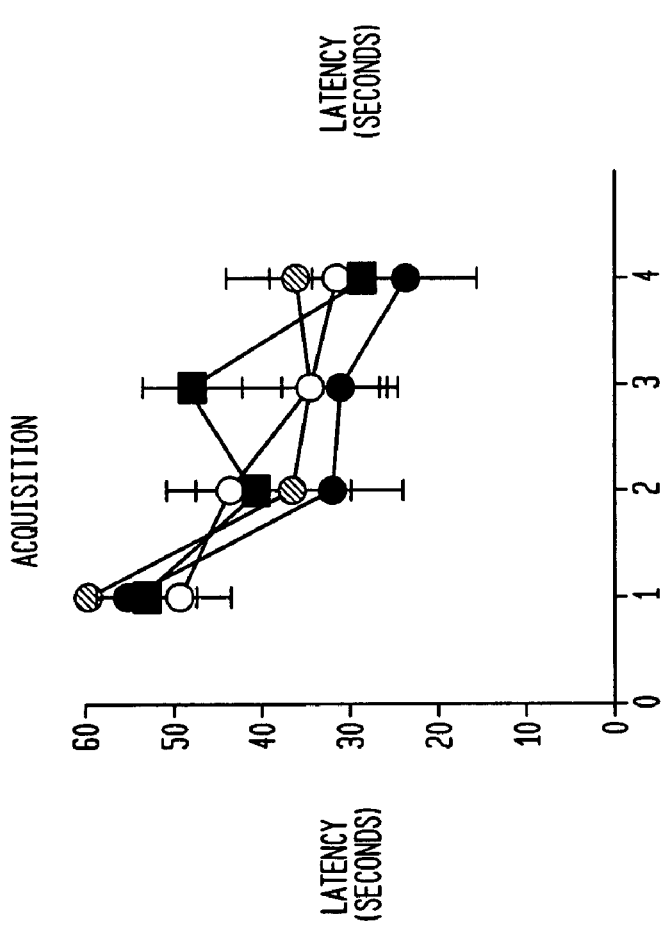
FIG. 3B
FIG. 3A

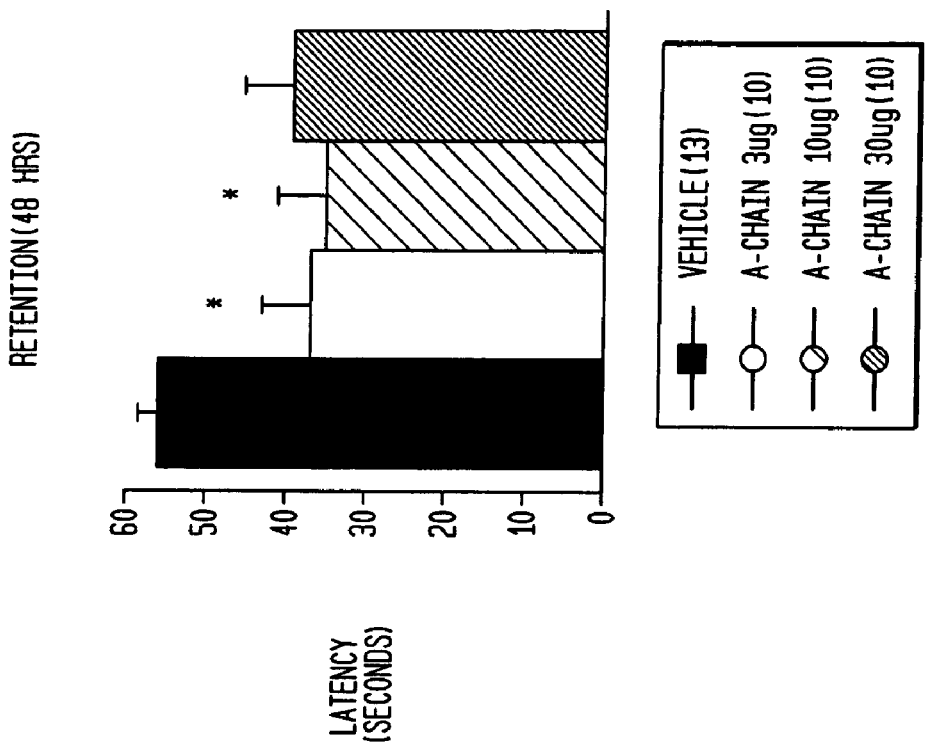
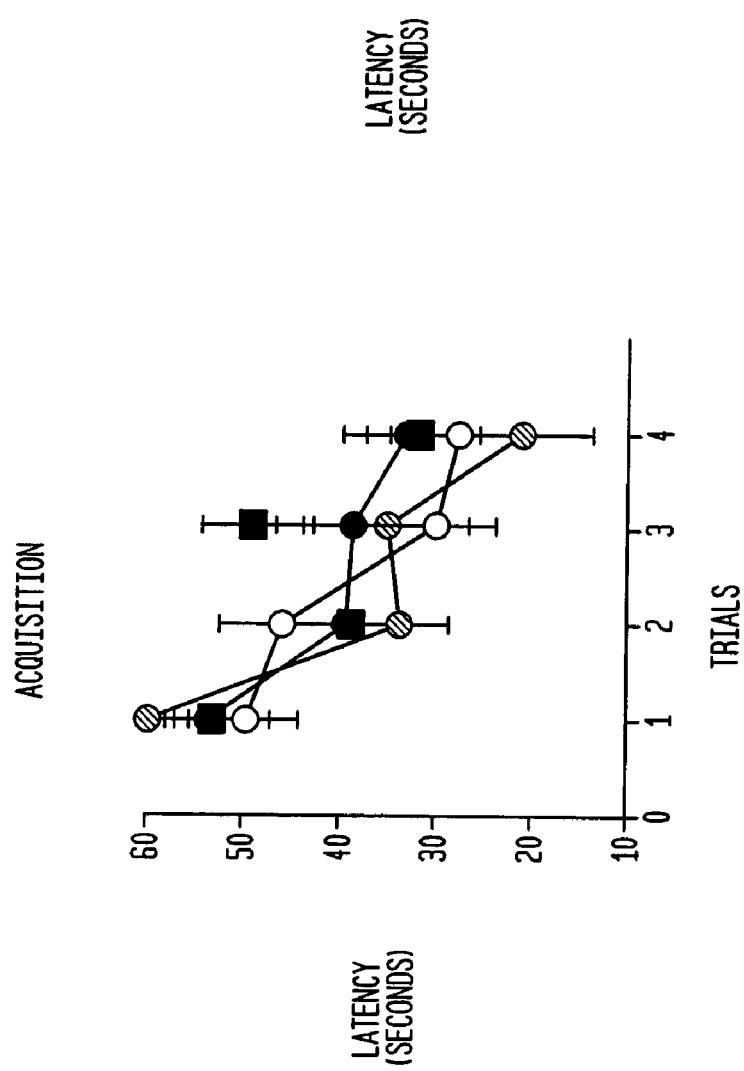

INSULIN-ASSOCIATED PEPTIDES WITH EFFECTS ON CEREBRAL HEALTH

PRIORITY

The present invention claims priority to U.S. Provisional Application No. 60/378,318 filed May 6, 2002, entitled "Insulin-Associated Peptides For Cerebral Health."

FIELD OF THE INVENTION

The present invention relates to the field of neurology, and in particular, the construction and use of peptides and their analogs with cognitive enhancing activity.

BACKGROUND OF THE INVENTION

Approximately 80% of people over 30 complain of some degree of memory loss. Normal memory loss includes the misplacing an item or forgetting the name of a person that you just met. Memory loss associated with mild cognitive impairment (MCI), a condition characterized by a memory deficit, but not dementia, is more severe than normal memory loss and often involves continuing problems in delayed recall of information. Most individuals who eventually develop dementia go through a phase of mild cognitive impairment, and some individuals with MCI develop the clinical stages of Alzheimer's Disease (AD).

Dementia, a structurally-caused, permanent or progressive decline of intellectual function, is one of the most serious disorders facing the elderly population. Dementia, which normally results in a loss of short-term and/or long-term memory, interferes substantially with social as well as economic activities. Memory loss is not only characteristic of the normal aging process but also of many neurological disorders. The risk of dementia is correlated with age and doubles every five years after the age of 60. Studies report that up to 50% of people over the age of 85 are afflicted with this disorder. An estimated 60-80% of elderly nursing home residents are affected by this disease.

Notably, the various forms of dementia are attributable to different causes. Many neurological disorders, such as Alzheimer's disease, can lead to forms of dementia. For example, Alzheimer-type dementia has been attributed to specific cellular and histological degenerative processes resulting in brain atrophy and the loss of cells from the basal forebrain, cerebral cortex, and other brain areas. Stroke, head trauma, and epilepsy can also lead to memory impairment. Epilepsy, a brain disorder in which neurons signal abnormally, can cause strange sensations, emotions, and behavior, or sometimes convulsions, muscle spasms, and loss of consciousness.

MCI patients over the age of 65 develop Alzheimer's Disease, one of the most common forms of dementia, at a rate of 12-15% yearly, which greatly exceeds the 1% to 2% incidence in normal controls healthy people. Thus, early treatment of patients with MCI could prevent further cognitive decline, including development of Alzheimer's disease. Alzheimer's disease is a degenerative brain disorder that afflicts millions of people worldwide. Alzheimer's Disease can affect memory, mood, personality, and cognitive ability. As the average human life-span continues to increase, the number of people developing Alzheimer's Disease at some point in their lives is escalating rapidly. Currently, an estimated one in twenty people over the age of 65 are affected by some form of dementia. In persons over the age of 80, that number rises to one in five.

Existing medications for neurological disorders and memory weaknesses are not always well tolerated, nor have they been proven effective in alleviating symptoms of dementia and memory loss. In addition, drugs, such as anti-epileptic drugs, can interfere with the effectiveness of other medications, such as oral contraceptives. Furthermore, while gingko biloba, piracetam, and various other "smart drugs" are being actively marketed, no proven memory-enhancing drug exists.

With the increasing lifespan of people, the lack of drugs that treat the biochemical causes of neurological disorders and memory impairment is becoming an acute problem. Thus, there exists a need in the art for drugs that can alleviate MCI, dementia and improve cognition and memory.

SUMMARY OF THE INVENTION

The present invention provides compositions and methods for ameliorating neurological, attention, or memory disorders and improving learning and cognition through the delivery of insulin A-chain and analogs thereof to a subject. Insulin A-chain, peptides comprising the 21 amino acid sequence GIVEQ CCASV CSLYQ LENYC N (SEQ ID NO:1), and functional analogs thereof are disclosed to modulate neurological activity when administered to a subject. The methods of the invention can be used to prevent or treat neurological disorders as well as improve memory retention and acquisition. The invention includes pharmaceutical compositions comprising a therapeutically or prophylactically effective amount of insulin A-chain peptide or a functional analogs thereof.

In one aspect, the present invention provides methods and compositions to ameliorate, slow the progression, or delay onset of a neurological disorder. In one embodiment, the neurological disorders include, but are not limited to, memory disorders, head injury, spinal cord injury, seizure, stroke, epilepsy and ischemia. Such neurological disorders include neurodegenerative disorders such as, but not limited to, epilepsy, Huntington disease, Parkinson's disease, attention deficit disorder (ADD), neuropsychiatric syndromes, Amyotrophic lateral sclerosis (ALS), and Alzheimer's disease (AD). Further neurological disorders include central nervous system (CNS) damage resulting from infectious diseases such as viral encephalitis, bacterial or viral meningitis and CNS damage from tumors. In another embodiment, the invention discloses a method of ameliorating a neurological disorder in a subject comprising administering to the subject a pharmaceutical composition comprising a therapeutically effective amount of an A-chain peptide or functional analog thereof, such that the A-chain peptide or functional analog thereof modulates the activity of a tyrosine kinase coupled receptor.

In another aspect, the present invention discloses a method for ameliorating a memory disorder in a subject, comprising administering to a subject a therapeutically effective amount of an insulin A-chain peptide or functional analog thereof, such that the administration of the insulin A-chain peptide or functional analog produces an amelioration of the memory disorder. In one embodiment, the method further comprises administering a therapeutically effective amount of an insulin A-chain peptide or functional analog thereof prior to onset of the memory disorder. In yet another embodiment, the administration of a therapeutically effective amount of an A-chain peptide or functional analog thereof increases memory retention in-the subject. The invention discloses a method for preventing or delaying the onset of a memory disorder in a subject, the method comprising administering to the subject a prophylactically effective amount of insulin A-chain or analog thereof, in a pharmaceutically acceptable carrier.

In another aspect, the compositions and methods of the present invention can be used to reduce memory disorders. A memory disorder refers to a diminished level of mental registration, retention or recall of past experiences, knowledge, ideas, sensations, thoughts or impressions. Memory disorders may affect short and long-term information retention, facility with spatial relationships, memory (rehearsal) strategies, and verbal retrieval and production. The compositions and methods of the present invention can be used to ameliorate memory disorders including, but not limited to, enhancing memory performance, improving or increasing the mental faculty by which to register, retain or recall past experiences, knowledge, ideas, sensations, thoughts, or impressions. In one embodiment, the present invention can be used for the treatment of mild cognitive impairment (MCI). Treating MCI early in the disease can decrease progression to Alzheimer's Disease (AD).

In a preferred embodiment, the methods and compositions of the present invention can be used to treat or reduce Alzheimer's disease. Alzheimer's disease (AD) is a degenerative brain disease, the incidence of which rapidly increases with advancing age. Certain populations of brain cells progressively die. Recently modern imaging techniques have revealed how the medial temporal lobe area, which contains the hippocampus (a vital structure for learning and memory generally in humans and for certain types of spatial learning in animals) progressively shrinks as Alzheimer's disease progresses.

This invention supports and encompasses the use of insulin A-chain peptides and analogs as potent and long lasting cognitive-enhancing drugs. The effect of insulin A-chain is evident 24 hours after administration of the peptide and is still present one week after a single administration. Moreover, administration of insulin A-chain peptides and analogs do not lead abnormal behavior, locomotor activities, or effects on blood glucose and, thus, appears to be specific for memory enhancement.

The present invention discloses a pharmaceutical composition comprising a pharmaceutically acceptable carrier and a therapeutically effective amount of the purified Achain peptide comprising SEQ ID NO. 1 or functional analog thereof, or said sequence with conservative amino acid substitutions. In one embodiment, a pharmaceutical composition of Achain or analog thereof can be delivered to a subject. As demonstrated in the present invention, the peptide can be delivered to a subject without systemic metabolic side effects despite homology to part of the insulin molecule. The peptide was shown to have no general neurological effects on activity, feeding, or anxiety as tested in the elevated plus maze and infrared locomotor boxes. As disclosed herein, the present invention lacks systemic and central toxicity while demonstrating apparent specificity for an orphan insulin-related receptor, which is highly expressed in the brain.

The method of administering a therapeutically effective amount of an insulin A-chain peptide or functional analog can be selected from the group comprising intraperitoneal, intracerebroventricular, intradernal, intramuscular, intravenous, subcutaneous, and intranasal. In a preferred embodiment, a therapeutically effective amount of an insulin A-chain peptide or functional analog is delivered by intranasal administration. Intranasal delivery of the peptide will allow it to efficiently enter the brain. Intranasal delivery of the peptide was shown, in the present invention, to lead to enhanced performance in a passive avoidance task and also to dramatically improve spatial learning as tested in the Morris Water Maze.

BRIEF DESCRIPTION OF THE FIGURES

FIG. 1 is a schematic of human insulin showing the 21 amino acids of insulin A chain (SEQ ID NO:3) and the 30 amino acids of insulin B-chain SEQ ID NO:4;

FIG. 2 is a bar graph of mean (±S.E.M.) latencies using a one-trial passive avoidance procedure showing that pretreatment with intra-nasal (3-30 μg, 28 USP units/mg) insulin significantly ($P<0.05$) enhanced associative learning in rats at the 10 μg dose compared to vehicle (5% (2,6-DI—O-methyl) β-cyclodextrin) alone;

FIG. 3A is a graph of mean (±S.E.M.) latencies of rats to find a submerged platform in the Morris Water Maze Paradigm following administration of insulin (3-30 μg, 28 USP units/mg) or vehicle (5% (2,6-DI—O-methyl)β-cyclodextrin) intra-nasally and trained for four trials demonstrating that acquisition times were not affected by insulin administration;

FIG. 3B is a bar graph of mean (±S.E.M.) latencies of rats to find a submerged platform in the Morris Water Maze Paradigm following administration of insulin (3-30 μg, 28 USP units/mg) or vehicle (5% (2,6-DI—O-methyl)β-cyclodextrin) intra-nasally demonstrating that retention times improved following administration of insulin;

FIG. 4 is a bar graph of blood glucose concentrations demonstrating that intra-nasal insulin administration of insulin A-chain (3-30 μg, 28 USP units/mg) produced no significant difference on blood glucose levels compared to control (vehicle (5% (2,6-DI—O-methyl)β-cyclodextrin));

FIG. 5 is a bar graph of mean (±S.E.M.) latencies using a one-trial passive avoidance procedure showing that pretreatment with intra-nasal A-chain (3-30 μg significantly **($F=10.005(3,37)$;$P<0.001$) enhanced latency attributable to associative learning at all doses tested compared to vehicle alone;

FIG. 6A is a graph of mean (±S.E.M.) latency to find a submerged platform in the Morris Water Maze Paradigm following administering A-chain (3-30 μg) or vehicle (5% 2.6-DI-Omthyl)β-cyclodextrin) intra-nasally showing no significant differences in acquisition between the groups during training;

FIG. 6B is a bar graph of mean (±S.E.M.) latency to find a submerged platform in the Morris Water Maze Paradigm following administering A-chain (3-30 μg) or vehicle (5% 2.6-DI-Omthyl)β-cyclodextrin) intra-nasally measured 48 hours following training demonstrating that 3 μg and 10 μg doses ($P<0.05$*) of A-chain significantly improved retention times and yielded significantly lower latency compared to vehicle alone;

FIG. 7 is a bar graph of mean (±S.E.M.) latencies using a one-trial passive avoidance procedure prior to which rats were administered doses of B-chain (3-30 μg) intranasally demonstrating that pretreatment with intra-nasal B-chain (3-30 μg) did not significantly ($F=0.906(3,39)$; $P=0.447$) enhance latency times compared to control (vehicle only);

FIG. 8A is a graph of mean (±S.E.M.) latency to find a submerged platform in the Morris Water Maze Paradigm of rats that received B-chain (3-30 μg) or vehicle (5%(2,6-DI-Omthyl)β-cyclodextrin) intra-nasally showing no significant differences in acquisition time between the groups during training;

FIG. 8B is a bar graph of mean (±S.E.M.) latency to find a submerged platform in the Morris Water Maze Paradigm of rats that received B-chain (3-30 µg) or vehicle (5%(2,6-DI-Omthyl)β-cyclodextrin) intra-nasally showing no significant differences in retention times between the groups;

Figure 11:
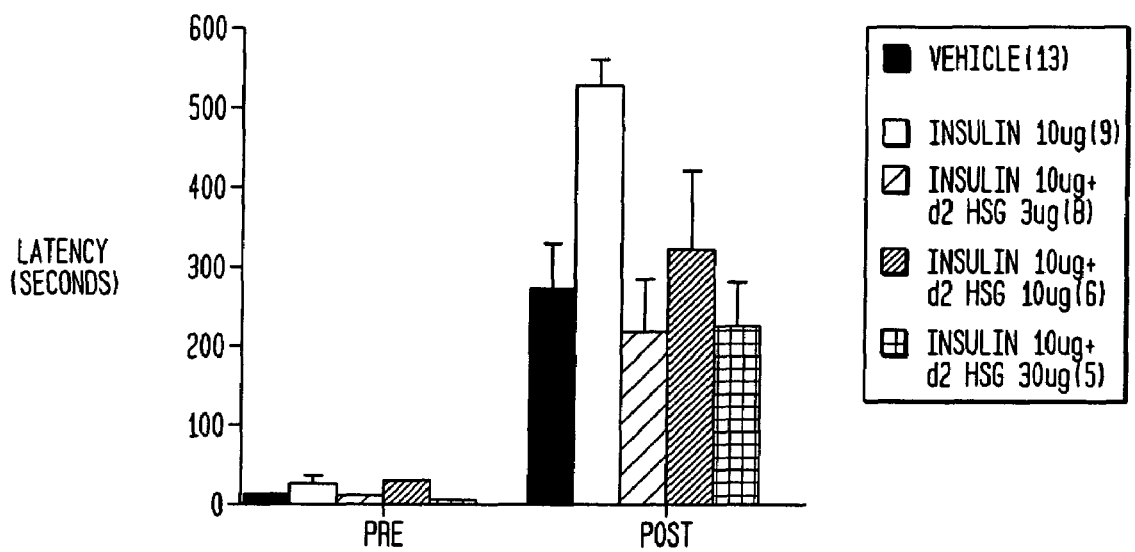
Figure 12:
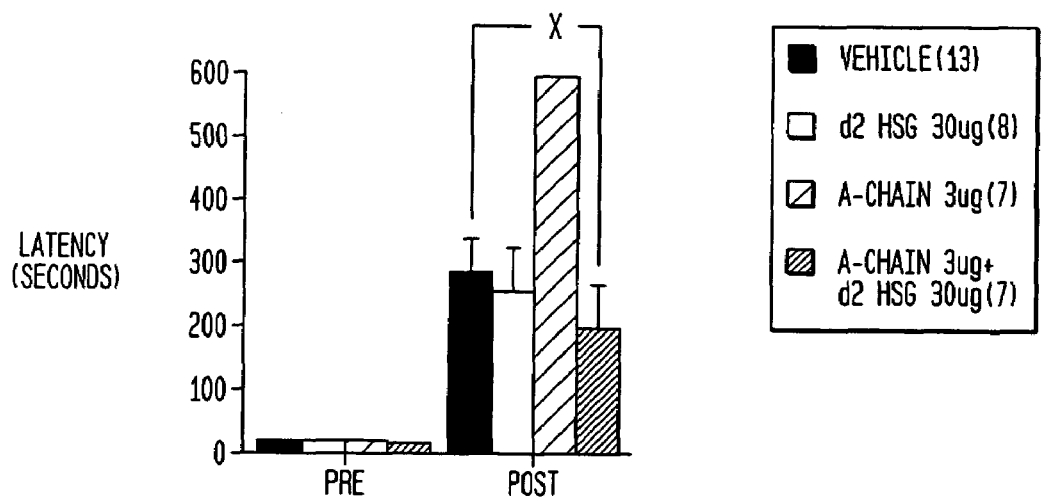

FIG. 11 is a bar graph of mean (±S.E.M.) latencies using a one-trial passive avoidance procedure showing that pretreatment with intranasal insulin (10 µg) alone significantly ($P<0.05$) enhanced latency time compared to vehicle alone while pretreatment with various doses of intranasal the insulin antagonist α 2 HS-Glycoprotein (α2HSG) (3-30 µg) in combination with insulin (10 µg) blocked enhancement of latency times by insulin ($F=3.700(4,35); P=0.01$); and FIG. 12 is a bar graph showing mean (±S.E.M.) latencies using a one-trial passive avoidance procedure showing that pretreatment with intra-nasal A-chain (3 µg) alone significantly ($t=4.634(21); P<0.01$) enhanced latency time compared to vehicle alone and pretreatment with α2HSG (30 µg) blocked enhancement of latency times by A-chain ($t=6.345(15); P<0.01$).

DETAILED DESCRIPTION

The present invention concerns the construction and use of peptides and their derivatives with cognitive enhancing and/or neuroprotective activity. The practice of the present invention employs methods of molecular biology, neurology, and peptide synthesis.

So that the invention may more readily be understood, certain terms are defined:

The terms "A-chain," and "insulin A-chain," as used interchangeably herein, refer to a neurological disorder ameliorating factor of any origin, which is substantially homologous and functionally equivalent to peptides comprising GIVEQ CCASV CSLYQ LENYC N (SEQ ID NO: 1) or peptides comprising SEQ ID NO: 1 with conservative amino acid or non-amino acid substitutions, or functional truncations or addition fragments thereof as described below. The sequence of insulin A-chains encompassed by this definition are well known in the art. Non-limiting examples of mammalian A-chain sequences include, but are not limited to, bovine A-chain (SEQ ID NO:1), porcine A-chain (SEQ ID NO:9), human A-chain (SEQ ID NO:3), mouse A-chain (SEQ ID NO 10), sheep A-chain (SEQ ID NO:11), rabbit A-chain (SEQ ID NO:12), monkey A-chain (SEQ ID NO:13), canine A-chain (SEQ ID NO 14), which can be found at GenBank Accession Nos. P01317, P01315, P01308, P01325, P01318, P01311, P30407, and P0132 1, respectively. The term A-chain is intended to cover A-chain with conservative amino acid substitutions that result in memory enhancing activity as demonstrated by the present invention. The term A-chain is intended to cover endogenous insulin A-chain in both vertebrates and invertebrates. Insulin is a two-chain polypeptide hormone produced by the β-cells of pancreatic islets having a molecular weight of approximately 5800 Da. The α(or A) and β(or B) chains are joined by two interchain disulfide bonds. The A-chain contains an intrachain disulfide bond. Insulin is involved in the regulation of the cellular uptake, utilization, and storage of glucose, amino acids and fatty acids as well as the inhibition of the breakdown of glycogen, protein and fat. Insulin A-chain peptides may exist as monomers, dimers or other multimers in their biologically active form. Thus, the term "A-chain" as used herein encompasses active monomeric A-chain, as well as active multimeric A-chain, active glycosylated and non-glycosylated forms of A-chain, active truncated forms of the molecule, and active larger peptides comprising SEQ ID NO: 1. The term A-chain is intended to include peptides comprising SEQ ID NO: 1 that have been post-translationally modified. By "functionally equivalent" as used herein, is meant an A-chain peptide that retains some or all of the neurological disorder ameliorating properties, but not necessarily to the same degree, as a native A-chain peptide. A-chain peptides or analogs thereof can be less than 50 amino acids in length. A-chain peptides or analogs thereof can be less than 40 amino acids in length, preferably less than 30 amino acids in length, preferably less than 20, more preferably less than 15 amino acids in length. More preferably, A-chain peptides or analogs thereof can be less than 12 amino acids in length, preferably less than 9 amino acids in length. Most preferably, A-chain peptides or analogs thereof can be less than 22 amino acids in length. Methods for making polynucleotides encoding for A-chain peptides or analogs thereof are known in the art and are described further below.

"Homology" refers to the percent similarity between two polynucleotide or two polypeptide moieties. Two polynucleotide, or two polypeptide sequences are "substantially homologous" to each other when the sequences exhibit at least about 50%, preferably at least about 75%, more preferably at least about 80%-85%, preferably at least about 90%, and most preferably at least about 95%-99% or more sequence similarity or sequence identity over a defined length of the molecules. As used herein, substantially homologous also refers to sequences showing complete identity to the specified polynucleotide or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis of similarity and identity, such as ALIGN, Dayhoff, M. O. in Atlas of Protein Sequence and Structure M. 0. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence similarity and identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent similarity of a particular nucleotide sequence to a reference sequence can be determined using the homology algorithm of Smith and Waterman with a default scoring table and a gap penalty of six nucleotide positions.

Another method of establishing percent similarity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence similarity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=1 0; Matnx=BLOSUM62; Descriptions50 sequences; sort by=HIGH SCORE; Databases=non-redundant, GenBank +EMBL+DDBJ+PDB+GenBank CDS translations+Swiss protein+Spupdate+PIR.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

In the present invention, the terms "analogs," "derivatives," or fragments" are used interchangeably to mean a chemical substance that is related structurally and functionally to another substance. An analog, derivative, or fragment contains a modified structure from the parent substance, in this instance, the biological function or activity of insulin A-chain, in cellular and animal models. The biological activity of the analog may include an improved desired activity or a decreased undesirable activity. The analog need not, but can be, synthesized from the other substance. For example, an insulin A-chain analog means a compound structurally related to insulin A-chain, but not necessarily made from insulin A-chain. Analogs of the instant invention, include, but are not limited to, analogs of insulin A-chain or a synthetic peptide that is substantially homologous to insulin A-chain. The term insulin A-chain analog is intended to cover insulin A-chain homologs including, but not limited to, fragments of insulinlike growth factor I (GenBank Acc. No. X03563), insulin-like growth factor II (ILGF-II) (GenBank Acc. No. X03562), INSL3 or Leydig insulin-like peptide or relaxin-like factor (GenBank Acc. No. X73637), insulin-like peptides, relaxin (GenBank Acc. Nos. X00949, X00948, BD103236, V00577, V00578), early placenta insulin-like growth factor (pro-EPIL) (GenBank Acc. No. Q14641) (Barnett and Owens, "Insulin analogues" *Lancet* Jan. 4, 1997 349(9044):47-51), (Kumagai et al. *J Biol. Chem* Aug. 30, 2002; 277(35): 31283-31286), (Brandt et al. *Cancer Res* Feb. 15, 2002; 62(4): 1020-1024), (Li et al. *Int J Exp Diabetes Res* 2002 October-December; 3(4):241-245)). The term analog is intended to include peptides derived from various members of the insulin superfamily including, but not limited to, insulin, relaxin, insulin-like growth factors I and II, mammalian Leydig cell-specific insulin-like peptide (gene INSL3), and early placenta insulin-like peptide (EPIL) (gene INSL4), insect prothoracicotropic hormone (bombyxin), locust insulin-related peptide (LIRP), molluscan insulin-related peptides 1 to 5 (MIP), and *C. elegans* insulin-like peptides, the sequences of which are known in the art (see for example, Claey et al. *Peptides* 2002, 23: 807-816). In their active forms, these peptide hormones are composed of two chains, the A-chain and B-chain, linked by two disulfide bonds. The arrangement of four cysteines is conserved in the A-chain, where Cys1 is linked by a disulfide bond to Cys3, Cys2 and Cys4 are linked by interchain disulfide bonds to cysteines in the B-chain (Schwabe et al. *FASEB J.* 1994 November; 8(14): 1152-60, Blundell et al. *Nature* Oct. 30, 1980;287(5785): 781-7, Murray-Rust et al. *Bioessays* 1992 May;14(5):325-31; Bedarkar et al. *Nature* Dec. 1, 1977;270 (5636):449-51).

The term "analog" as used herein, further refers to a biologically active derivative of the A-chain peptide, or a fragment of such a derivative, that retains desired activity, such as increased memory retention activity in the assays described herein. In general, the term "analog" as used herein, is intended to mean functional derivatives or fragments that is related structurally and functionally to another substance. An analog contains a modified structure from the parent substance, in this case insulin A-chain, and substantially maintains the function of the parent substance, in this instance, the biological function or activity of insulin A-chain in cellular and animal models. The biological activity of the analog may include an improved desired activity or a decreased undesirable activity. The analog need not, but can be synthesized from the other substance. The analog can be chemically or recombinantly synthesized using methods known in the art, for example, GenBank Accession No. J02544. For example, an A-chain analog can be a compound structurally related to insulin A-chain, but not necessarily comprising the same amino acids as human insulin A-chain. In general, the term "analog" refers to compounds having a native polypeptide sequence and structure with one or more amino acid additions, substitutions (generally conservative in nature) and/or deletions, relative to the native molecule, so long as the modifications do not destroy the memory enhancing activity. Preferably, the analog has at least the same memory enhancement activity as the native molecule. The term analog is intended to include peptides comprising the SEQ ID NO:1 with one or more amino acid substitutions (preferably conservative) as well as peptides comprising the SEQ ID NO:1 with amino acid or non-amino acid substitutions to the sequence. A-chain peptides or analogs thereof can be less than 50 amino acids in length. A-chain peptides or analogs thereof can be less than 40 amino acids in length, preferably less than 30 amino acids in length, preferably less than 20, more preferably less than 15 amino acids in length. More preferably, A-chain peptides or analogs thereof can be less than 12 amino acids in length, preferably less than 9 amino acids in length. Most preferably, A-chain peptides or analogs thereof can be less than 22 amino acids in length. Methods for making polynucleotides encoding for A-chain peptides or analogs thereof are known in the art and are described further below.

For A-chain addition analogs, amino acid sequence additions typically include N-and/or C-terminal fusions ranging in length from one residue to polypeptides containing a hundred or more residues, as well as internal additions of single or multiple amino acid residues. Internal additions generally range from about 1-10 residues, more typically from about 1-5 residues, and usually from about 1-3 amino acid residues, or any integer within the stated ranges. Examples of N-terminal addition variants include the fusion of a heterologous N-terminal signal sequence to the N-terminus of A-chain as well as fusions of amino acid sequences derived from the sequence of other neuroprotective factors.

A-chain substitution analogs have at least one amino acid residue of SEQ ID NO:1 removed and a different residue inserted in its place. Such substitution variants include allelic variants, which are characterized by naturally occurring nucleotide sequence changes in the species population that may or may not result in an amino acid change. Particularly preferred substitutions are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity.

For example, the A-chain molecule may include up to about 10 conservative or non-conservative amino acid substitutions, or preferably up to about 5 conservative or non-conservative amino acid substitutions, so long as the desired function of the molecule remains intact. One having ordinary skill in the art may readily determine regions of the molecule of interest that can tolerate change using techniques well known in the art.

The term "A-chain analog" means an active A-chain polypeptide as defined above or below having at least about 50% amino acid sequence identity with a full-length native sequence A-chain polypeptide sequence as disclosed herein, or any other fragment of a full-length A-chain polypeptide sequence as disclosed herein. Such A-chain polypeptide variants include, for instance, A-chain polypeptides wherein one or more amino acid residues are added, or deleted, at the N- or C-terminus of the full-length native amino acid sequence. Ordinarily, an A-chain polypeptide variant will have at least about 50% amino acid sequence identity, alternatively at least about 55% amino acid sequence identity, alternatively at least about 60% amino acid sequence identity, alternatively at least about 65% amino acid sequence identity, alternatively at least about 70% amino acid sequence identity, alternatively at least about 75% amino acid sequence identity, alternatively at least about 80% amino acid sequence identity, alternatively at least about 85% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence A-chain polypeptide sequence as disclosed herein, or any other specifically defined fragment of a full-length A-chain polypeptide sequence as disclosed herein. Ordinarily, A-chain analog polypeptides are at least about 6 amino acids in length, alternatively at least about 10 amino acids in length, alternatively at least about 15 amino acids in length, alternatively at least about 20 amino acids in length, alternatively at least about 25 amino acids in length, alternatively at least about 30 amino acids in length, alternatively at least about 35 amino acids in length, alternatively at least about 40 amino acids in length, alternatively at least about 45 amino acids in length, alternatively at least about 50 amino acids in length, alternatively at least about 55 amino acids in length, alternatively at least about 60 amino acids in length, alternatively at least about 65 amino acids in length, or more.

The term "percent (%) amino acid sequence identity" with respect to the A-chain polypeptide sequences identified herein is defined as the percentage of amino acid residues in a candidate sequence that are identical with the amino acid residues in the specific A-chain polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

Percent amino acid sequence identity values may be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the A-chain analog of interest having a sequence derived from the native A-chain peptide and the comparison amino acid sequence of interest (i.e., the sequence against which the A-chain analog of interest is being compared which may be an A-chain variant polypeptide) as determined by WU-BLAST-2 by (b) the total number of amino acid residues of the A-chain analog of interest. For example, in the statement "a polypeptide comprising the amino acid sequence A which has or having at least 80% amino acid sequence identity to the amino acid sequence B", the amino acid sequence A is the comparison amino acid sequence of interest and the amino acid sequence B is the amino acid sequence of the A-chain analog of interest.

Percent amino acid sequence identity may also be determined using the sequence comparison program NCBI-BLAST2 (Altschul et al., Nucleic Acids Res. 25:33 89-3402 (1997)). The NCBI-BLAST2 sequence comparison program may be downloaded or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "ameliorate," as used herein, is intended to mean improve, lessen, inhibit, delay onset of and/or otherwise modulate a disorder.

As used herein, the term "A chain peptide" or "A-chain polypeptide," as used interchangeably, refer to a functional or active analog, derivative or fragment of insulin A-chain containing naturally occurring amino acids, non-naturally occurring amino acids or chemically modified amino acids, provided that the compound retains the bioactivity or function of insulin A-chain.

As used herein, the term "amino acid" refers to one of the twenty naturally occurring amino acids, including, unless stated otherwise, L-amino acids and D-amino acids. The term amino acid also refers to compounds such as chemically modified amino acids including amino acid analogs, naturally occurring amino acids that are not usually incorporated into peptides such as norleucine, and chemically synthesized compounds having properties known in the art to be characteristic of an amino acid, provided that the compound can be substituted within a peptide such that it retains its biological activity. For example, glutamine can be an amino acid analog of asparagine, provided that it can be substituted within an active fragment, derivative or analog of A-chain that retains its bioactivity or function in cellular and animal models. Other examples of amino acids and amino acids analogs are listed in Gross and Meienhofer, The Peptides: Analysis, Synthesis, Biology, Academic Press, Inc., New York (1983), which is incorporated herein by reference. An amino acid also can be an amino acid mimetic, which is a structure that exhibits substantially the same spatial arrangement or functional groups as an amino acid but does not necessarily have both the α-amino and α-carboxyl groups characteristics of an amino acid.

The terms "functional" or "bioactive," as used interchangeably herein, mean a peptide having a chemical structure that mimics the structure of A-chain and retains at least 50% of the bioactivity and function of insulin A-chain in cellular and animal models. The function may include an improved desired activity or a decreased undesirable activity. Such a mimetic generally is characterized as exhibiting similar physical characteristics such as size, charge or hydrophobicity in the same spatial arrangement found in insulin A-chain or the insulin-like peptide counterpart. A specific example of a peptide mimetic is a compound in which the amide bond between one or more of the amino acids is replaced, for example, by a carbon-carbon bond or other bond well known in the art (see, for example, Sawyer, Peptide Based Drug Design, ACS, Washington (1995), which is incorporated herein by reference). Non-limiting tests for a functional insulin A-chain are disclosed below. The peptides of the present invention are intended to be functional in at least one bioactivity assay. Specifically, when the peptide is subject to in vivo and/or in vitro testing conditions, a modification results. Tests for functionality are described in the Examples section of the specification. For example, an increase in memory retention can result following the addition of the peptide.

The terms "neurological disorder" or "CNS disorder," as used interchangeably herein, refer to an impairment or absence of a normal neurological function or presence of an abnormal neurological function in a subject. For example, neurological disorders can be the result of disease, injury, and/or aging. As used herein, neurological disorder also includes neurodegeneration which causes morphological and/or functional abnormality of a neural cell or a population of neural cells. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurological disorders include, but are not limited to, memory disorders, head injury, spinal cord injury, seizures, stroke, dementia, memory loss, attention deficit disorder (ADD), epilepsy, and ischemia. Neurological disorders also include neurodegenerative diseases. Neurodegeneration can occur in any area of the brain of a subject and is seen with many disorders including, but not limited to, Amyotrophic Lateral Sclerosis (ALS), multiple sclerosis, Huntington's disease, Parkinson's disease and Alzheimer's disease.

Further neurological disorders include CNS (central nervous system) damage resulting from infectious diseases such as viral encephalitis, bacterial or viral meningitis and CNS damage from tumors. The neuroprotective and/or neural regenerative strategy of the present invention can be also be used to improve the cell-based replacement therapies used to treat or prevent various demyelinating and dysmyelinating disorders, such as Pelizaeus-Merzbacher disease, multiple sclerosis, various leukodystrophies, post-traumatic demyelination, and cerebrovasuclar accidents. Disorders of the central nervous system further include mental disorders such as mood disorders (i.e., depression, bipolar disorder), anxiety disorders, memory disorders and schizophrenic disorders. In addition, the present invention may also find use in enhancing the cell-based therapies used to repair damaged spinal cord tissue following a spinal cord injury.

The term "memory disorder," as used herein, refers to a diminished mental registration, retention or recall of past experiences, knowledge, ideas, sensations, thoughts or impressions. Memory disorder may affect short and/or long-term information retention, facility with spatial relationships, memory (rehearsal) strategies, and verbal retrieval and production. The term memory disorder is intended to include dementia, slow learning and the inability to concentrate. Common causes of a memory disorder are age, severe head trauma, brain anoxia or ischemia, alcoholic-nutritional diseases, drug intoxications, and neurodegenerative diseases. For example, a memory disorder is a common feature of neurodegenerative diseases, such as Alzheimer's disease (i.e. Alzheimer-type dementia). Memory disorders also occur with other kinds of dementia such as AIDS Dementia; Wernicke-Korsakoffs related dementia (alcohol induced dementia); age related dementia, multi-infarct dementia, a senile dementia caused by cerebrovascular deficiency, and the Lewy-body variant of Alzheimer's disease with or without association with Parkinson's disease. Creutzfeldt-Jakob disease, a spongiform encephalopathy caused by the prion protein, is a rare dementia with which memory disorder is associated. Loss of memory is also a common feature of brain-damaged patients. The term memory disorder is intended to cover mild cognitive impairment (MCI), which is a condition characterized by loss of memory, but no other symptoms of dementia, such as problems with language or personality or behavior changes. Patients with MCI are at high risk to develop other neurological diseases, such as Alzheimer's Disease. Non-limiting examples of causes of brain damage which may result in a memory disorder include stroke, seizure, an anaesthetic accident, ischemia, anoxia, hypoxia, cerebral edema, arteriosclerosis, hematoma or epilepsy; spinal cord cell loss; and peripheral neuropathy, head trauma, hypoglycemia, carbon monoxide poisoning, lithium intoxication, vitamin (B1, thiamine and B12) deficiency, or excessive alcohol use. Korsakoffs amnesic psychosis is a rare disorder characterized by profound memory loss and confabulation, whereby the patient invents stories to conceal his or her memory loss. It is frequently associated with excessive alcohol intake. Memory disorder may furthermore be age-associated; the ability to recall information such as names, places and words seems to decrease with increasing age. Transient memory loss may also occur in patients, suffering from a major depressive disorder, after electro-convulsive therapy.

The term "therapeutically effective amount" refers to an amount effective, at dosages and for periods of time necessary, to achieve the desired therapeutic result. A therapeutically effective amount of insulin A-chain peptide may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The term "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

The term "subject" as used herein refers to any living organism capable of eliciting an immune response. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "pharmaceutically acceptable carrier" as used herein, refers to a carrier that is conventionally used in the art to facilitate the storage, administration, and/or the biological activity of a regulatory agent. A carrier may also reduce any undesirable side effects of the regulatory agent. A suitable carrier should be stable, i.e., incapable of reacting with other ingredients in the formulation. It should not produce significant local or systemic adverse effect in recipients at the dosages and concentrations employed for treatment. Such carriers are generally known in the art. Suitable carriers for this invention include those conventionally used for large stable macromolecules such as albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), cyclodextrin, 2, 6-DI—O-Methyl) β-cyclodextrin and the like. Water, saline, aqueous dextrose, and glycols are preferred liquid carriers, particularly (when isotonic) for solutions. The carrier can be selected from various oils, including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like. Other acceptable components in the pharmaceutical composition include, but are not limited to, isotonicity-modifying agents such as water, saline, and buffers including phosphate, citrate, succinate, acetic acid, and other organic acids or their salts. Typically, the pharmaceutically acceptable carrier also includes one or more stabilizers, reducing agents, anti-oxidants and/or anti-oxidant chelating agents. The use of buffers, stabilizers, reducing agents, anti-oxidants and chelating agents in the preparation of protein-based compositions, particularly pharmaceutical compositions, is well known in the art. See, Wang et al. (1980) *J. Parent. Drug Assn.* 34(6): 452-462; Wang et al.(1988) *J. Parent. Sci. Tech.* 42:S4-S26 (Supplement); Lachman et al.(1968) *Drug and Cosmetic Industry* 102(1):36-38, 40, and 146-148; Akers (1988) *J. Parent. Sci. Tech.* 36(5):222-228; and *Methods in Enzymology*, Vol. XXV, ed. Colowick and Kaplan, "Reduction of Disulfide Bonds in Proteins with Dithiothreitol," by Konigsberg, pp. 185-188.

Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. See Wang (1980) supra at page 455. Suitable salts and isotonicifiers include sodium chloride, dextrose, mannitol, sucrose, trehalose, or the like. Where the carrier is a liquid, it is preferred that the carrier is hypotonic or isotonic with oral, conjunctival, or dermal fluids and has a pH within the range of 4.5-8.5. Where the carrier is in powdered form, it is preferred that the carrier is also within an acceptable non-toxic pH range.

Suitable reducing agents, which maintain the reduction of reduced cysteines, include dithiothreitol (DTT also known as Cleland's reagent) or dithioerythritol at 0.01% to 0.1% wt/wt; acetylcysteine or cysteine at 0.1% to 0.5% (pH 2-3); and thioglycerol at 0.1% to 0.5% (pH 3.5 to 7.0) and glutathione. See Akers (1988) supra at pages 225-226. Suitable antioxidants include sodium bisulfite, sodium sulfite, sodium metabisulfite, sodium thiosulfate, sodium formaldehyde sulfoxylate, and ascorbic acid. See Akers (1988) supra at page 225. Suitable chelating agents, which chelate trace metals to prevent the trace metal catalyzed oxidation of reduced cysteines, include citrate, tartarate, ethylenediaminetetraacetic acid (EDTA) in its disodium, tetrasodium, and calcium disodium salts, and diethylenetriamine pentaacetic acid (DTPA). See, e.g., Wang (1980) supra at pages 457-458 and 460-461, and Akers (1988) supra at pages 224-227.

I. Insulin

Insulin is a peptide hormone known to regulate various physiological functions such as blood glucose, food intake and body weight via peripheral and central receptors (Woods et al., 1979, *Nature*, 282:503-505, Bruning et al., 2000, *Science*, 289:2122-2125, Schwartz et al., 2000, *Nature*, 404:661-671). The structure of insulin has been determined for at least 100 vertebrate species. In addition to the four invariant cysteines, only ten other amino acids appear to be conserved. These invariant amino acids comprise GlyAl, IleA2, ValA3, TyrA19, LeuB6, GlyB8, LeuB11, ValB12, GlyB23, and PheB24 (Conlon, J M *Peptides* 2001, 22(7): 1183-1193). The insulin molecule is composed of two peptide chains referred to as A-chain and B-chain. The A and B chains are linked together by two disulfide bonds; an additional disulfide is formed within the A-chain. The B-chain has been shown to have a wide variety of physiological effects whereas the A-chain has not (Song et al. 1999, *Diabetes Res Clin Pract*, 46:109-114). A majority of studies using insulin have focused on its role in diabetes and glucose regulation. Recent evidence, however, shows that insulin enhances learning and memory.

The present invention is based, in part, on the identification that the 21 amino acid insulin A-chain enhances acquisition and retention of memory. A small peptide that retains the essential bioactivity is preferable since it is more stable and would be able to more easily pass through the blood-brain barrier (BBB). In this invention, A-chain peptides and analogs are shown to have cognitive-enhancing efficacy following peripheral administration (See Examples).

A. Insulin Superfamily

Insulin gene superfamily hormones regulate cell growth, metabolism, and tissue-specific functions. The insulin superfamily groups a number of active peptides which are evolutionary related including insulin, relaxin, insulin-like growth factors I and II, mammalian Leydig cellspecific insulin-like peptide (gene INSL3), and early placenta insulin-like peptide (ELIP) (gene INSL4), insect prothoracicotropic hormone (bombyxin), locust insulin-related peptide (LIRP), molluscan insulin-related peptides 1 to 5 (MIP), and *C. elegans* insulin-like peptides. In their active forms, these peptide hormones are composed of two chains, the A-chain and B-chain, linked by two disulfide bonds. The arrangement of four cysteines is conserved in the A-chain, where Cys1 is linked by a disulfide bond to Cys3, Cys2 and Cys4 are linked by interchain disulfide bonds to cysteines in the B-chain (Schwabe et al. *FASEB J.* 1994 November;8(14):1152-60, Blundell et al. *Nature* Oct. 30, 1980;287(5785):781-7, Murray-Rust et al. *Bioessays* 1992 May; 14(5):325-31; Bedarkar et al. *Nature* 1977 Dec 1;270(5636):449-51). In one aspect of the present invention, an A-chain or functional analog of the insulin superfamily can be used to ameliorate a neurological disorder.

Figure 1:
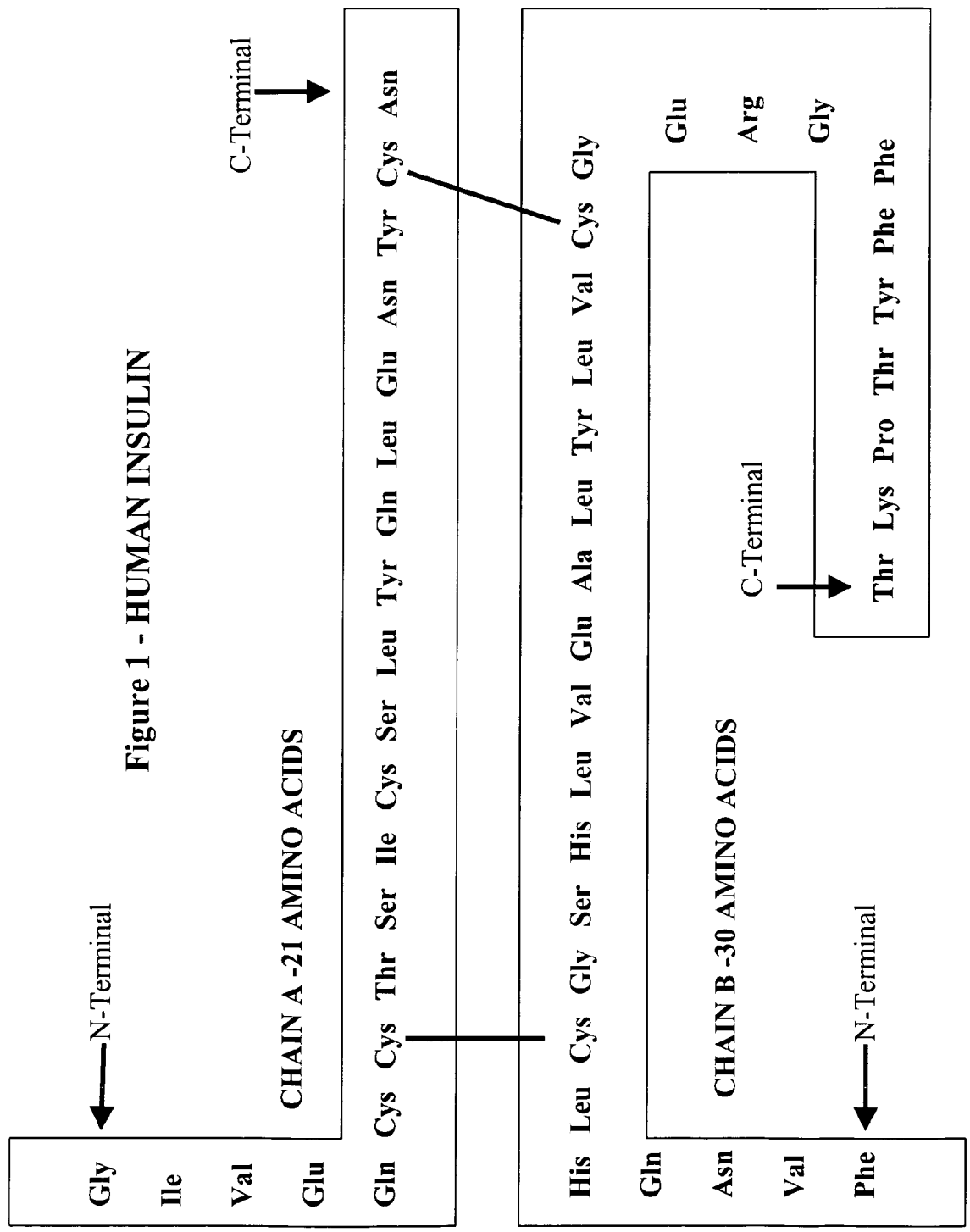

Human insulin, illustrated in FIG. 1, is a non-steroidal hormone comprising two polypeptide chains (A and B). In all vertebrates, the A-chain comprises 21 amino acid residues and the B-chain comprises 30 amino acid residues. The A- and B-chains are joined by two intermolecular disulfide bridges at A7-B7 cysteines and at the A20-B19 cysteines. A third intramolecular disulfide bridge is formed within the A-chain between A6-A11 cysteines. Human insulin is naturally produced in the pancreas by the beta-cells of the islets of Langerhans, via a single 110 amino acid precursor polypeptide (preproinsulin) (Chan, S. J. et al., 1976, *Proc. Natl. Acad. Sci. USA*, 73: 1964-1968; Sheilds and Blobel, 1977, *Proc. Natl. Acad. Sci.* USA, 74: 2059-2063) with a structure of: ($NH_2$) pre-peptide-B-chain-C-peptide-A-chain (COOH) The INS gene maps to 11p14.1 (Chaganti et al. *Somat. Cell Molec. Genet.* 11: 197-202, 1985). Approximately 16 mutant forms of human insulin, which can contain up to 4 amino acids changes, have been found to be endogenously produced by the human pancreas.

The human preproinsulin (precursor) undergoes various post-translational modifications and events to convert it into mature insulin. The first step is removal of the prepeptide (Bell, G. I. et al., 1979, *Nature* 282: 525-527), which acts as a signal sequence to direct the molecule (proinsulin) upon synthesis into the endoplasmic reticulum (ER) and hence into the secretory pathway. After entry into the ER, the resultant proinsulin then folds and the three disulfide bridges are formed. The proinsulin then passes to the Golgi, is packaged into secretory granules and is converted into mature insulin by endoproteolytic cleavage (Steiner, D. F. et al., 1984, *J. Cell. Biol.*, 24: 121-130).

A human source of insulin has always been impractical due to low yields from the pancreas and degradation. However, the structure of insulin is highly conserved in other mammals, making it possible to use other animals as a source of insulin. For example, bovine and porcine insulin differ from human insulin in three and one amino acids respectively, but generally both can be used for human medication. This has led to the development of porcine and bovine insulins. Many synthetic insulin homologues have been developed. For example, humulin, which is produced by recombinant DNA technology, is structurally identical to human insulin but is slower acting. A newer, faster synthetic insulin, humalog, has been developed by switching specific lysine and proline or substituting the Asp for Pro residues, to improve solubility (See Novo Nordisk). Recombinant DNA methods have allowed the synthesis of various forms of recombinant human insulin. This has been achieved using *E. coli* and *Saccharomyces cerevisiae*. Early techniques involved the production of separate A- and B-chains (Goeddel, D., et al., 1979, *Proc. Natl. Acad. Sci. USA*, 76: 106-110; Chance, R. E. et al., 1981, In: Rich, D. H. & Gross, E. (eds.) Peptides: Synthesis-Structure-Function, Proc. Seventh American Peptide Symposium, pp 721-728, Rockford II, Pierce Chemical Co.; Frank, B. H. et al., 1981, In. Rich, D. H. & Gross, E. (eds.) Peptides: *Synthesis-Structure-Function*, Proc. Seventh American Peptide Symposium, pp 729-738. Rockford II, Pierce Chemical Co.; Steiner, D. F., et al., 1968, *Proc. Natl. Acad. Sci. USA*, 60: 622; and EP-A-0 090 433).

B. Insulin Receptor in the CNS

Once considered an insulin-independent organ, recent evidence demonstrates that insulin and associated molecular machinery within the brain plays an important physiological role and may be vital in learning and memory processes. Following the identification of insulin in the mammalian central nervous system, research has focused on the role of this peptide in the central nervous system. The biological role for insulin action in energy homeostasis and appetite regulation and diabetes mellitus is well established. However, insulin not only plays a role in energy metabolism, but also in the function of the central nervous system.

Evidence suggests that insulin is produced in the adult brain, but not in great amounts. Central concentrations of insulin are procured from circulating peptides that gains entry into the CNS through a specific transport mechanism (Schwartz et al. *Am J Physiol*, 1990, E378-83; Banks et al. *Peptides* 1997, 28:1257-1262). Insulin may also be translocated through the hypothalamus or by way of circumventricular organs such as the median eminence where endothelial cells lack the tight junctions seen in the blood brain barrier. High levels of insulin receptors are distributed throughout the CNS specifically in neurons (Unger et al. *Prog Neurob* 1991, 36: 343-362). Particularly dense concentrations are present in the hippocampus—a structure that mediates learning and memory (Havrankova et al. *Nature* 1978, 272: 827-829; Unger et al. *Neuroscience* 1989; 31: 143-157; Unger et al. *Neuroscience* 1991, 36: 343-362). Within the hippocampus, insulin binding has been detected, for example, in the dentate gyrus as well as in the CA1 pyramidal cells, and is associated with phosphotyrosine and insulin receptor substrate-1 (IRS-1) (Baskin et al. *Endocrinology* 1994, 134: 1952-1955). Insulin receptors are highly localized in the limbic system, particularly within the hippocampus; a brain area critically involved in learning and memory processes and the medial temporal region (Havrankova et al., 1978, *Nature*, 272:827-829, Werther et al. 197 *Endocrinology*, 121:1562-1570, Sara et al., *Neuralscience Letters*, 34:39-44).

Insulin receptor localization profiles in the brain suggest that insulin may have cognitive enhancing properties and that disruption of insulin receptors, or their lack of activation, may result in decrements in learning. Indeed, profound deficits in learning and memory have been observed in drug-induced diabetic animals (Biessels et al. 1996, *Diabetes*, 45:1259-1266) and in humans with type 1 and type 2 diabetes (Ryan 1988, *Diabetes Care*, 11(1):86-93; Ott et al. 1999, *Neurology*, 53(9):1937-42). Moreover, cerebrospinal insulin and insulin receptor levels have been shown to decline with age (Frolich et al. 1998, *Journal of Neural Transmission*, 105:423-438), and individuals with dementia have significantly higher insulin plasma levels (Stolk et al. 1997, *Diabetes Care*, 20:792-795). Further, hyperinsulinemia in non-diabetic individuals is associated with cognitive impairment (Kalmijn et al. 1995, *Diabetologia*, 38:1096-1102). This increase in plasma insulin is hypothesized to be due to abnormalities in insulin transport from periphery to brain (Craft et al. 1998, *Neurology*, 50:164-

168; Frolich et al 1998, *Journal of Neural Transmission*, 105:423-438). Interestingly, in cases of sporadic Alzheimer's disease, insulin receptor-transduction mechanisms are compromised (Frolich et al. 1999, *Annals of the New York Academy of Sciences*, 893:290-293). And, consistent with the above-mentioned studies, cerebrospinal fluid insulin levels of individuals with Alzheimer's disease are lower, but plasma levels higher, compared to controls (Craft et al. 1998, *Neorology*, 50:164-168). Furthermore, intravenous insulin administration has been shown to reverse Alzheimer's-associated diminution in memory (Craft et al., 1999, *Arch Gen Psychiatry*, 56(12):1135-40).

While full-length insulin has been implicated in learning and memory, the portion of the molecule that causes this activity had not been discovered prior to this invention. The present invention illustrates that 21 amino acid A-chain can modify learning and memory. According to this invention, an A-chain and/or functional analogs can ameliorate neurological disorders when administered to a subject. In one embodiment, the methods and compositions of the present invention can ameliorate memory disorders. The present invention demonstrates that an insulin A-chain has potent memory enhancing effects (see Example 4 and 5). The insulin A-chain and functional analogs may be used to facilitate learning, memory and cognition in mammals. The insulin A-chain and functional analogs also may be used to treat nervous system disorders associated with impaired learning, memory and cognition in mammals. Furthermore, the insulin A-chain and functional analogs may be used to treat nervous system or neurological disorders associated with neuronal loss or dysfunction, including, but not limited to, Parkinson's Disease, Alzheimer's Disease, Huntington's Disease, ALS, stroke, attention deficit disorder (ADD) and neuropsychiatric syndromes, in mammals.

Alpha 2-Heremans Schmid Glycoprotein (alpha-2-HSG), or human fetuin, is an endogenous inhibitor of insulin receptor tyrosine kinase activity (IR-TKA) and has been shown to inhibit the mitogenic pathway without affecting the metabolic portion of insulin signal transduction. $\alpha$2HSG is a potent inhibitor of insulin-induced tyrosine phosphorylation of Shc, an intra-cellular protein involved in the insulin signaling pathway. As shown in Example 6, the insulin agonist $\alpha$2HSG blocks the facilitation of associative learning by insulin and insulin A-chain demonstrating that the effects associated with administration of insulin A-chain are linked to a tyrosine kinase coupled receptor. In one embodiment, insulin A-chain and derivatives interact with a tyrosine kinase coupled receptor expressed in the brain. Experiments done using cell lines transduced with insulin or IGF receptors suggest that the A-chain peptide does not act through the insulin receptor nor the IGF receptor. Thus, the insulin A-chain or analog thereof can be a ligand for an orphan insulin-receptor related receptor which is highly expressed in the brain.

Upon binding full-length insulin, the insulin receptor undergoes autophosphorylation. At least two isoforms of the insulin receptor have been identified (Ullich et al. *Nature* 1985, 313: 756-761). Once activated, the insulin receptor then phosphorylates IRS-proteins and She resulting in activation of Grb2/SOS and the Ras/Raf/Mek/MAPK pathway. The insulin signaling pathway involves well studied proteins such as, but not limited to, IRS (insulin receptor substrate), She protein, phosphatidylinositol (PI)-kinase, PKB (protein kinase B). The receptor for insulin A-chain in the brain can be found using methods known in the art, such as in situ experiments following administration of labeled A-chain. In yet another embodiment, A-chain or analog can interact with a down stream receptor or protein involved in insulin signaling, such as Shc.

For activation, the insulin receptor requires IRSs (insulin receptor substrates 1-3). These substrates are components of synapses within the central nervous system and probably play a role in intracellular signaling. IRS-1 and insulin mRNA message are colocalized in neuronal hippocampal cell bodies and olfactory bulb whereas protein levels are concentrated in dendritic and synaptic projections of these neurons (Baskin et al. *Endocrinology* 1994, 134: 1952-1955). Studies indicate that five of the conserved amino acids in the insulin molecule (IleA2, ValA3, TyrA19, GlyB23, and PheB24) may interact directly with the insulin receptor whereas the other invariant amino acids, LeuB6, GlyB8, LeuB 11, GluB13, and PheB25, are likely to maintain the receptor-binding conformation (Conlon, J M *Peptides* 2001, 22(7): 1183-1193). While the specific identity of the tyrosine kinase receptor implemented by this invention to interact with A-chain peptides and analogs in the brain to ameliorate neurological disorders has not been identified, it is possible that A-chain amino acids IleA2, ValA3, and TyrA19 may be important for binding. Thus, in one embodiments, analogs can be made such that the three amino acids IleA2, ValA3, and TyrA19 remain.

Stimulation of the insulin receptor appears to culminate in activation of the Ras-dependent mitogen-activated protein kinase (MAPK) cascade which plays a pivitol role in long-term memory processes. In addition to insulin's potent cognitive enhancing properties on its own, this peptide modulates a variety of neurotransmitters that play a key role in learning and memory processes. For example, insulin blocks the reuptake of norepinephrine in synaptosome preparations dissociated brain cells and neuronal cultures. Sauter et al. (*Brain Res* 1983 260: 330-333) showed using hypothalamic slices that insulin induces increases in the release of central catecholamines. Streptozotocin-induced hypoinsulinemia results in altered norepinephrine transporter and tyrosine hydroxylase mRNA—the rate limiting enzyme in catecholamine synthesis. Moreover, streptozotocin-induced diabetes decreases epinephrine and dopamine in certain brain areas (Park et al. 2001 *Physiol Behav* 2000 68: 509-514).

In one embodiment, A-chain and analogs interact in the hippocampus resulting in an amelioration of a neurological disorder. This interaction can ameliorate memory disorders. Insulin is known to exert effects in the hippocampus. Stimulation of $\alpha_1$-adrenergic receptors in the hippocampus by insulin results in the accumulation of inositol phosphate which activates PKC; a kinase involved in the intracellular cascade that is vital in learning and memory.

II. Memory Enhancement

In one aspect, the present invention provides methods and compositions for ameliorating memory disorders. Thus, the compositions and methods of the present invention can be used to prevent, delay onset, or treat memory disorders. The present invention can increase mental registration, retention or recall of past experiences, knowledge, ideas, sensations, thoughts or impressions. In a preferred embodiment, the present invention increases short and/or long-term information retention, facility with spatial relationships, memory (rehearsal) strategies, and verbal retrieval and production. Insulin A-chain peptides and analogs have been shown to increase both associative learning and spatial memory (Examples 4 and 5).

Learning and memory in animals, both vertebrates and invertebrates, involves what is commonly termed synaptic plasticity, i.e., a mechanism by which a given input is associated with enhanced or facilitated output. The most commonly established physiological model of such learning is long term potentiation (LTP), by which repeated excitatory pulses, i.e., titanic stimuli, lead to a long lasting potentiation of the stimulated synapse. The molecular mechanism of this synaptic potentiation and plasticity is starting to be unraveled, with the data suggesting a change in gene expression mediated via transcriptional activation. The transcription factors with the most convincing and supportive data are members of the cyclic AMP (cAMP) responsive element binding protein (CREB) family. Loss of plasticity and impaired learning and memory have been demonstrated in studies involving the delivery of mutant CREB in model systems as well as studies of CREB knockout mice. Conversely, activating CREB or overexpressing CREB has been shown to induce a super-learning phenotype. Furthermore, cAMP response element binding protein (CREB) has been shown to be essential in the conversion of short- to long-term memory (Fox, K. *Neuroscience,* 2002, 111(4): 799-814; Zhang et al. *Neuroscience* 2003 117(3) 707-713; Scott R et al. *J Mol Neurosci* 2002 19(1-2):171-177). In summary, cAMP regulated CREB, and CREB may regulate the expression of the transcription factor, Zif268, whose expression is triggered by LTP and learning (See, for example, Silva A J. *J Neurobiol* 2003 54(1):224-237). Thus, according to this invention, A-chain peptides and functional analogs thereof can lead to an increase in cAMP.

There are a large number of endogenous peptides that have effects on learning and memory in mammalian model systems. These include vasoactive intestinal protein (VIP), vasopressin or anti-diuretic hormone (ADH), and corticotrophin releasing hormone (CRH). Each of these native peptides, however, retains pleiotropic actions, including influences on neuroendocrine function, as well as potential anxiogenic or arousal effects that are likely to limit any potential applications. Moreover, these peptides generally are only effective if directly delivered into the central nervous system (CNS).

The MAPK family consists of key regulatory proteins that are known to regulate cellular responses to both proliferative and stress signals. MAPKs consist of several enzymes, including a subfamily of extracellular signal-activated kinases (ERK1 and ERK2) and stress-activated MAPKs. There are three distinct groups of MAPKs in mammalian cells: a) extracellular signalregulated kinases (ERKs), b) c-Jun N-terminal kinases (JNKs) and c) stress activated protein kinases (SAPKs).

PKC activation or other factors (e.g. increases in free intracellular $Ca^{2+}$) activates small proteins called Ras/Raf-1, which in turn activate MAPK/ERK kinases referred to as MEKs. The MEKS in turn activate ERKs. The ERKS translocate to the cell nucleus where they activate transcription factors and thereby regulate cell proliferation. The modulation of these protein kinases produces neuroprotective and neuron-treating effects as does the modulation of the MAPK cascade. Examples of such kinases are mitogen-activated protein kinase 1 and 2, their homologues and isoforms, extracellular signal-regulated kinases (ERKs) their homologues and isoforms (ERK1, ERK2, ERK3, ERK4), and a group of kinases known as MAP/ERK kinases 1 and 2 or MEK1/2.

Exposure of cells to stress activates protein kinases by a variety of mechanisms. For example, ischemia, NMDA (N-methyl-D-aspartate) and amyloid peptides activate MAPK. Studies of functional roles of MAPKs in nerve tissue suggest that MAPK could be an important regulator of nerve cell death and plasticity. Thus, MAPK activation is required for hippocampal long-term potentiation (LTP). A-chain peptides and analogs of the present invention may increase MAP kinase production, secretion, and/or activity in the brain or A-chain peptides and analogs may activate the extracellular signal-regulated protein kinase (ERK)/mitogen-activated protein kinase (MAP) kinase pathway with nuclear translocation of p42 MAP kinase, which is associated with long-term memory.

Thus, the compositions and methods of the present invention can improve hippocampal-dependent learning. In one embodiment, the compositions and methods of the present invention can improve associative learning. In another embodiment, the compositions and methods of the present invention can improve spatial memory. As shown in Examples 4 and 5, the effects of centrally administered A-chain on associative learning and spatial memory, both of which are hippocampal dependent, were investigated using the passive avoidance (PA) and Morris Water Maze (MWM) paradigms in rats. A-chain administered intranasally enhanced latency in the PA task compared to B-chain and vehicle only control. Assessment of the effects of A-chain on spatial memory in the MWM showed that the peptide significantly reduced the time to locate the platform compared to control rats 48 hours following training.

Central administration of drugs poses major problems for translation to clinical applications. The potential for side-effects caused by systemic administration can be averted by nasal delivery (Born J, et al. *Nat Neurosci.* 2002 Jun;5(6): 514-6). The regions of the brain that mediate working memory also control of impulses and motor activity. As shown in Example 4 and 5, intranasal administration of A-chain peptides and analogs increased latency in the PA test. No toxic systemic effects were observed. A-chain did not affect blood glucose levels nor locomotor activity as shown in Examples 3 and 7.

III. A-Chain Peptides and Analogs

In one embodiment, A-chain peptides comprising SEQ ID NO:1 and active analogs thereof can be synthesized with amino-acid and non-amino acid residues that are capable of improving pharmaceutical relevant properties, such as, but not limited to, solubility, stability, and lipophilicity. In a preferred embodiment, A-chain can be synthesized with a stearic acid residue (e.g. free fatty acid, adamantane, or dihydropyridine) added to the N terminus to improve lipophilicity. Additional amino acid and non-amino acid substitutions are well-known in the art and are discussed above. Biological activity of A-chain peptides and analogs can be confirmed as described in the Examples section.

The present invention relates to A-chain and to variations of the A-chain peptide that show the biological activity or function of A-chain. This biological activity or function may include an improved activity or a decreased undesirable activity. Functional assays for A-chain are described below in the Examples section. Such variants of A-chain include functional analogs, derivatives, fragments, and mimetics of A-chain. The invention further includes methods for selecting functional analogs, fragments, and mimetics of A-chain from a collection of randomly obtained or rationally designed candidate compounds. Compounds selected by the process described herein will retain the biological activity or function of A-chain.

The fragments, derivatives, analogs, or mimetics of the A-chain peptide may be: (1) one in which one or more of the amino acid residues are substituted with a conserved or non-conserved amino acid residue; (2) one in which one or more of the amino acid residues includes a substituent group; (3) one in which the mature peptide is fused with another compound, such as a compound to increase the half-life of the peptide (for example, polyethylene glycol); (4) one in which the additional amino acids are fused to the mature peptide, such as a leader or secretory sequence or a sequence that is employed for purification of the mature peptide or a prepeptide sequence; or (5) one which comprises fewer or greater amino acid residues than has SEQ. ID. NO:1 and yet still retains activity characteristics of A-chain. Such fragments, derivatives, analogs, and mimetics are deemed to be within the scope of those skilled in the art from the teachings herein.

The present invention is intended to include homologous A-chains. In one aspect, the A-chain or analog of relaxin can be used to ameliorate neurological disorders. Relaxin is synthesized and stored in the corpora lutea of ovaries during pregnancy and is released into the blood stream prior to parturition. The availability of ovaries has enabled the isolation and amino acid sequence determination of relaxin from different species, such as pig, rat, and shark. The biologically active hormone consists of two peptide chains (known as the A and B chains) held together by disulphide bonds, two inter-chain and one intra-chain. The structure thus closely resembles insulin in the disposition of disulphide bonds which has led to speculation of a common ancestral gene for these hormones (James et al, *Nature,* 267, 544-546 (1977). For example, a sequence of human relaxin HI, which is useful for the present invention, comprises RPYVA LFEKC CLIGX CTKRS LAKYC (SEQ ID NO: 2). Analogs of SEQ ID NO: 2 are encompassed by the present invention.

Recombinant DNA techniques have been applied to the isolation of cDNA clones for both rat and porcine relaxins (Hudson et al. *Nature,* 291, 127-131 (1981), see also Australian Patent Application No. 11834/83 (PF 2696/82). The relaxin structural gene was found to code in both cases for a single chain precursor which resembles preproinsulin in the overall configuration, i.e., signal peptide/B chain/C peptide/A-chain. Australian Patent Application No. 17906/83 (No. PF 5352/82, filed 12th Aug., 1982) describes the molecular cloning and characterization of a gene sequence coding for human relaxin. U.S. Pat. No. 4,758,516 discloses the genes and DNA transfer vectors for the expression of human prorelaxin, preprorelaxin and the A and/or B and/or C peptide chains of human relaxin. In another aspect, the A-chain of insulin-like proteins can be used to ameliorate neurological disorders. Insulin-like protein (INSL3, INSL4, INSL5, INSL6 & INSL7/H3 Relaxin) belongs to the insulin-like hormone superfamily, which encompasses insulin, relaxin, and insulin-like growth factors I (IGF1) and II (IGF2).

A. Identification of A-Chain Analogs

One skilled in the art may prepare such fragments, derivatives, analogs, or mimetics of the A-chain peptide by modifying the native sequence by resultant single or multiple amino acid substitutions, additions, or deletions. These changes are preferably of a minor nature, such as conservative amino acid substitutions, that do not significantly affect the folding or activity of the peptide. For instance, one polar amino acid, such as threonine, may be substituted for another polar amino acid, such as serine; or one acidic amino acid, such as asparatic acid, may be substituted for another acidic amino acid, such as glutamic acid; or a basic amino acid, such as lysine, arginine, or histidine, may be substituted for another basic amino acid; or a non-polar amino acid, such as alanine, leucine or isoleucine, may be substituted for another non-polar amino acid. Guidance concerning which amino acid changes are likely to be phenotypically silent can be found in Bowie, J. U., et al., *"Deciphering the Message in Protein Sequences: Tolerance to Amino Acid Substitutions,"* Science 247:1305-1310 (1990). Of course, the number of amino acid substitutions a skilled artisan would make depends on many factors.

Moreover, A-chain amino acids that are essential for function can be identified and variations can be made using methods known in the art, such as oligonucleotide-mediated (sit-edirected) mutagenesis, alanine scanning, and PCR mutagenesis. Site-directed mutagenesis (Carter et al., *Nucl. Acids Res.,* 13:4331 (1986); Zoller et al., *Nucl. Acids Res.,* 10:6487 (1987)) cassette mutagenesis (Wells et al., *Gene,* 34:315 (1985)), restriction selection mutagenesis (Wells et al., Philos. *Trans. R. Soc. London SerA,* 317:415 (1986)) or other known techniques can be performed on the cloned DNA to produce A-chain variant DNA.

One well-known method for identifying A-chain amino acid residues or regions for mutagenesis is known as "alanine scanning mutagenesis." See, e.g., Cunningham and Wells, *Science* (1989) 244:1081-1085. In this method, an amino acid residue or group of target residues are identified (e.g., charged residues such as Arg, Asp, His, Lys, and Glu) and replaced by a neutral or negatively charged amino acid (most preferably alanine or polyalanine) to affect the interaction of the amino acids with the surrounding aqueous environment in or outside the cell. Those domains demonstrating functional sensitivity to the substitutions are refined by introducing additional or alternate residues at the sites of substitution. Thus, the target site for introducing an amino acid sequence variation is determined, alanine scanning or random mutagenesis is conducted on the corresponding target codon or region of the DNA sequence, and the expressed A-chain analogs are screened for the optimal combination of desired activity and degree of activity.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, *Science,* 244: 1081-1085 (1989)). Alanine is also typically preferred because it is the most common amino acid. Further, it is frequently found in both buried and exposed positions (Creighton, The Proteins, (W. H. Freeman & Co., N.Y.); Chothia, *J. Mol. Biol.,* 150:1 (1976)). If alanine substitution does not yield adequate amounts of variant, an isoteric amino acid can be used.

Initially, sites can be substituted in a relatively conservative manner. If such substitutions result in a change in biological activity, then more substantial changes (exemplary substitutions) are introduced, and/or other additions or deletions may be made, and the resulting products screened for activity. Non-conservative substitutions will entail exchanging a member of one of these classes for another class. Such substituted residues also may be introduced into the conservative substitution sites or, more preferably, into the remaining (non-conserved) sites.

Peptides of the present invention can be prepared in any suitable manner. Such peptides include isolated naturally occurring peptides, recombinantly produced peptides, synthetically produced peptides, or peptides produced by a combination of these methods. Means for preparing such peptides are well known in the art.

Peptides of the instant invention can be identified by screening a large collection, or library, of random peptides or peptides of interest. Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid that encodes it. Methods for the production of phage display libraries, including vectors and methods of diversifying the population of peptides that are expressed, are well known in the art (see, for example, Smith & Scott, *Methods Enzymol.* 217:228-257 (1993); Scott & Smith, *Science* 249:386-390 (1990); and Huse, WO 91/07141 and WO 91/07149, each of which is incorporated herein by reference). These or other well known methods can be used to produce a phage display library, from which the displayed peptides can be cleaved and assayed for activity, for example, using the methods disclosed infra. If desired, a population of peptides can be assayed for activity, and an active population can be subdivided and the assay repeated in order to isolate an active peptide from the population. Other methods for producing peptides useful in the invention include, for example, rational design and mutagenesis based on the amino acid sequences of active fragments of A-chain.

Studies have indicated that A-chain amino acids IleA2, ValA3, and TyrA19 may be important for binding. Thus, in one embodiments, analogs can be made such that the three amino acids IleA2, ValA3, and TyrA19 remain. Based on structure-activity relationships of the full-length insulin, the eighth amino acid of the A-chain (A8) or (ThrA8) amino acid has been identified as important for controlling the receptor-substrate affinity. Substitution analogs replacing ThrA8 with HisA8 or ArgA8 showed improved stability with substitution with LysA8 showed improved activity (Weiss et al. *J Mol Biol* 2002 315(2): 103-11). Thus, substitution analogs with HisA8 or ArgA8 or LysA8 amino acids are included in this invention. In addition, an insulin analog comprising SerA7, SerA20, and CysA6 and CysA11 (Le Flem et al. *Bioorg. Med. Chem.,* 2002, 10, 2111-2117) is included in this invention. Analogs comprising GIVEQ CCTSI CSLYQ LENYC N (SEQ ID NO: 3); the sequence of human insulin A-chain can be used in the present invention.

In addition, the sequences of additional A-chain peptides that are useful in the present invention including, but not limited to, guinea pig, *Cavia porcellus*, chinchilla, *Chinchilla brevicaudata*, casiragua, *Proechimys guairae*; coypu, *Myocastor coypus*; porcupine, *Hystrix cristata*; cuis, *Galea musteloides*, degu, *Octodon degus*; Teleostei: carp, *Cyprinus carpio*; pacu, *Piaractus mesopotamicus*; flounder, *Platichthys flesus*, tilapia, *Oreochromis nilotica*, anglerfish, *Lophius americanus*, cod, *Gadus callarias*; toadfish, *Opsanus tau*; sculpin, *Cottus scorpius*; coho salmon, *Oncorhynchus kisutch*; elephantnose, *Gnathonemus petersii*, eel, *Anguilla anguilla*; Lepisosteiformes: gar, *Lepisosteus spatula*; Amiiformes: bowfin, *Amia calva*; Acipenseriformes: paddlefish, *Polyodon spathula*; sturgeon, *Scaphirhynchus albus* and *Acipenser guldenstaedti*; Polypteriformes: bichir, *Polypterus senegalis*; Holocephali: ratfish, *Hydrolagus colliei*; rabbit-fish, *Chimaera monstrosa*; elephantfish, *Callorhynchus milii*; Elasmobranchii: electric ray, *Torpedo marmorata*; spiny dogfish, *Squalus acanthias*; spotted dogfish, *Scyliorhinus canicula*; hammerhead shark, *Sphyrna lewinii*; Agnatha: sea lamprey, *Petromyzon marinus*; river lamprey, *Lampetra fluviatilis*; Atlantic hagfish, *Myxine glutinosa* can be found in the art (See Conlon J. M. *Peptides* 2001 22: 1183-1193). In addition, the sequences of peptides belonging to the insulin superfamily that are useful in the present invention can be found in the art (See, Claey et al. *Peptides* 2002, 23: 807-816).

An active analog of A-chain, useful in the invention, can be isolated or synthesized using methods well known in the art. Such methods include recombinant DNA methods and chemical synthesis methods for production of a peptide. Recombinant methods of producing a peptide through expression of a nucleic acid sequence encoding the peptide in a suitable host cell are well known in the art and are described, for example, in Sambrook et al., Molecular Cloning: A Laboratory Manual, $2^{nd}$ Ed, Vols 1 to 3, Cold Spring Harbor Laboratory Press, New York (1989), which is incorporated herein by reference.

B. Generation of A-Chain and Analogs

A-chain peptides or functional analogs thereof useful in the invention also can be produced by chemical synthesis, for example, by the solid phase peptide synthesis method of Merrifield et al., *J. Am. Chem. Soc.* 85:2149 (1964), which is incorporated hereby by reference. Standard solution methods well known in the art also can be used to synthesize a peptide useful in the invention (see, for example, Bodanszky, Principles of Peptide Synthesis, Springer-Verlag, Berlin (1984) and Bodanszky, Peptide Chemistry, Springer-Verlag, Berlin (1993), each of which is incorporated herein by reference). A newly synthesized peptide can be purified, for example, by high performance liquid chromatography (HPLC), and can be characterized using, for example, mass spectrometry or amino acid sequence analysis.

In addition, functional analogs, derivatives, fragments or mimetics of A-chain can be synthesized by use of a peptide synthesizer. Furthermore, if desired, non-classical amino acids or chemical amino acid analogs can be introduced as a substitution or addition into the A-chain sequence. Non-classical amino acids include but are not limited to the D-isomers of the common amino acids, α-amino isobutyric acid, 4 amino-butyric acid, Abu, 2-amino butyric acid, γ-Abu, ϵ-Ahx, 6-amino hexanoic acid, Aib, 2-amino isobutyric acid, 3-amino propionic acid, omithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer aminoacids such as β-methyl amino acids, C-α-methyl amino acids, N-α-methyl amino acids, and amino acid analogs in general. Furthermore, the amino acid can be D (dextrorotary) or L (levorotary).

It is understood that limited modifications can be made to a functional analog, derivative, fragment or mimetic of A-chain without destroying its biological function. Thus, a modification of a functional analog, derivative, fragment or mimetic of A-chain that does not destroy its activity or function is within the definition of a functional analog, derivative, fragment or mimetic of A-chain. A modification can include, for example, an addition, deletion, or substitution of amino acid residues; a substitution of a compound that mimics amino acid structure or function; and addition of chemical moieties such as amino or acetyl groups.

A particularly useful modification is one that confers, for example, increased stability. For example, incorporation of one or more D-amino acids or substitution or deletion of lysine can increase the stability of an active analog, derivative, fragment or mimetic of A-chain by protecting against peptide degradation. The substitution or deletion of a lysine residue confers increased resistance to trypsin-like proteases, as is well known in the art (Partridge, Peptide Drug Delivery to the Brain, Raven Press, New York, 1991). These substitutions increase stability and, thus, bioavailability of peptides, but do not affect activity.

A useful modification also can be one that promotes peptide passage across the blood-brain barrier, such as a modification that increases lipophilicity or decreases hydrogen bonding. For example, a tyrosine residue added to the C-terminus of a peptide may increase hydrophobicity and permeability to the blood-brain barrier (see, for example, Banks et al., *Peptides* 13:1289-1294 (1992), which is incorporated herein by reference, and Pardridge, supra, 1991). A chimeric peptide-pharmaceutical that has increased biological stability or increased permeability to the blood-brain barrier, for example, also can be useful in the method of the invention.

Various methods of chemically synthesizing peptides are known, including solid-phase synthesis which, like peptide synthesis, has been fully automated in commercially available DNA synthesizers (See the Itakura et al. U.S. Pat. No. 4,598,049; the Caruthers et al. U.S. Pat. No. 4,458,066; and the Itakura U.S. Pat. Nos. 4,401,796 and 4,373,071). For example, nucleotide sequences greater than 100 bases long could be readily synthesized in 1984 on an Applied Biosystems Model 380A DNA Synthesizer as evidenced by commercial advertising of the same (e.g., Genetic Engineering News, November/December 1984, p. 3). Such oligonucleotides can readily be spliced using, among others, the techniques described later in this application to produce any nucleotide sequence described herein. For example, relatively short complementary oligonucleotide sequences with 3' or 5' segments that extend beyond the complementary sequences can be synthesized. By producing a series of such short segments, with "sticky" ends that hybridize with the next short oligonucleotide, sequential oligonucleotides can be joined together by the use of ligases to produce a longer oligonucleotide that is beyond the reach of direct synthesis. Furthermore, automated equipment is also available that makes direct synthesis of any of the peptides disclosed herein readily available. Such equipment provides ready access to the peptides of the invention, either by direct synthesis or by synthesis of a series of fragments that can be coupled using other known techniques.

In addition to the specific peptide sequences shown in SEQ. ID NO: 1, SEQ ID NO: 2 and SEQ ID NO: 3 and other peptides based on these sequence and representing variations thereof can have similar biological activities of A-chain. Additional exogenous amino acids can be present at either or both terminal ends of the core protein or its truncations. These added sequences can, for example, facilitate purification, or be used for in the generation of fusion proteins having novel activities.

Within the portion of the molecule containing the A-chain sequence, replacement of amino acids is more restricted in order that biological activity can be maintained. However, variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids.

In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatichydroxyl; (4) aromatic=phenylalanine, tyrosine, tryptophan; (5) amide=asparagine, glutamine; and (6) sulfur-containing=cysteine and methoinine. (see, for example, Biochemistry, 2nd ed, Ed. by L. Stryer, W H Freeman and Co.: 1981). Whether a change in the amino acid sequence of a peptide results in a functional A-chain sequence can readily be determined by assessing the ability of the corresponding DNA encoding the peptide to produce this peptide in a form containing an A-chain peptide when expressed by eukaryotic cells. Peptides in which more than one replacement has taken place can readily be tested in the same manner.

By "purified," it is meant, when referring to a peptide or DNA or RNA sequence, that the indicated molecule is present in the substantial absence of other biological macromolecules of the same type, such as other proteins. The term "purified" as used herein preferably means at least 80% by weight, more preferably at least 95% by weight, and most preferably at least 99% by weight, of biological macromolecules of the same type present (but water, buffers, and other small molecules, especially molecules having a molecular weight of less than 1000, can be present). The term "pure" as used herein preferably has the same numerical limits as "purified" immediately above. The term "isolated" as used herein refers to a peptide, DNA, or RNA molecule separated from other peptides, DNAs, or RNAs, respectively, that are present in the natural source of the macromolecule. "Isolated" and "purified" do not encompass either natural materials in their native state or natural materials that have been separated into components (e.g., in an acrylamide gel) but not obtained either as pure substances or as solutions.

Two protein sequences are homologous (as this term is preferably used in this specification) if they have an alignment score of >5 (in standard deviation units) using the program ALIGN with the mutation data matrix and a gap penalty of 6 (or greater). See Dayhoff, M. O., in Atlas of Protein Sequence and Structure, 1972, volume 5, National Biomedical Research Foundation, pp. 101-110, and Supplement 2 to this volume, pp. 1-10. The two sequences (or parts thereof—probably at least 30 amino acids in length) are more preferably homologous if their amino acids are greater than or equal to 50% identical when optimally aligned using the ALIGN program mentioned above. Two DNA sequences (or a DNA and RNA sequence) are homologous if they hybridize to one another using nitrocellulose filter hybridization (one sequence bound to the filter, the other as a $^{32}P$ labeled probe) using hybridization conditions of 40-50% formamide, 37°-42° C., 4×SSC and wash conditions (after several room temperature washes with 2×SSC, 0.05% SDS) of stringency equivalent to 37° C. with 1×SSC, 0.05% SDS.

Salts of any of the macromolecules described herein will naturally occur when such molecules are present in (or isolated from) aqueous solutions of various pHs. All salts of peptides and other macromolecules having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

The invention has specifically contemplated each and every possible variation of peptide that could be made by selecting combinations based on the amino acid sequence disclosed in SEQ. ID. Nos: 1, 2, and 3 and possible conservative amino acid substitutions and all such variations are to be considered as being specifically disclosed.

Included within the scope of the invention are active analogs, derivatives, fragments or mimetics of A-chain that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogens bromide, trypsin, chymotrypsin, papain, V8 protease, $NaBH_4$; acetylation, formylation, oxidation, reduction; metabolic synthesis in the presence of tunicamycin; etc. The terms "A-chain" and/or "A-chain peptide" as used herein are intended to encompasses not only the amino acid sequence (SEQ ID NO: 1) but also these various derivatives and modifications.

Moreover, the peptide of the present invention can be a chimeric, or fusion, protein comprising A-chain or an analog, derivative, fragment, or mimetic thereof joined at its amino- or carboxy-terminus via a peptide bond to an amino acid sequence of a different protein. In one embodiment, such a chimeric protein is produced by recombinant expression of a nucleic acid encoding the protein. Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

IV. Therapeutic uses

In one aspect of the invention, A-chain and analogs can be used for the therapeutic and prophylactic treatment of neurological disorders. Neurological disorder can be associated with neuronal loss or dysfunction, including, but not limited to, Parkinson's Disease, Alzheimer's Disease, Huntington's Disease, ALS, stroke, epilepsy, ADD, and neuropsychiatric syndromes. In one embodiment, the neurological disorder is a neurodegenerative disorder. In another embodiment, the neurological disorder is selected from the group comprising seizures, strokes, brain ischemia, and epilepsy. In a preferred embodiment, the neurological disorder is a memory disorder. The present invention can be used to ameliorate attention disorders. The regions of the brain that mediate working memory also regulate the capacity for sustained attention (i.e., vigilance).

Compounds of the instant invention are administered therapeutically (including prophylactically): (1) in diseases, disorders, or conditions involving neuronal loss or dysfunction, including, but not limited to, Parkinson's Disease, Alzheimer's Disease, Huntington's Disease, ALS, stroke, ADD, and neuropsychiatric syndromes; or (2) in diseases, disorders, or conditions wherein in vitro (or in vivo) assays indicate the utility of the peptides of the present invention.

Alzheimer's disease (AD) is a degenerative brain disease, the incidence of which rapidly increases with advancing age. Certain populations of brain cells progressively die, particularly but by no means exclusively those using acetylcholine as a neurotransmitter. Recently modern imaging techniques have revealed how the medial temporal lobe area, which contains the hippocampus (a vital structure for learning and memory generally in humans and for certain types of spatial learning in animals) progressively shrinks as Alzheimer's disease runs its course. The principle symptoms of Alzheimer's disease are steadily progressive loss of cognitive faculties such as memory (particularly recent episodic memories), problems with language and speech such as difficulty in finding the right words, and attention. Multi-infarct dementia, the most common other form of dementia, often presents a similar clinical picture but as it is due to a series of small strokes its progression is more stepwise. In one aspect of the invention, A-chain peptides or functional analogs can delay onset, ameliorate the symptoms, or treat Alzheimer's disease. In one embodiment, the methods and compositions of the present invention can be used to slow or stop the conversion from MCI to Alzheimer's disease.

In another aspect of the invention, A-chain and functional analogs can be used for the therapeutic and prophylactic treatment of memory disorders. A-chain and analogs can be used to ameliorate a memory disorder. Preferably, A-chain or analogs can improve learning and/or cognition. Memory disorder refers to a diminished mental registration, retention or recall of past experiences, knowledge, ideas, sensations, thoughts or impressions. Memory disorder may affect short and/or long-term information retention, facility with spatial relationships, memory (rehearsal) strategies, and verbal retrieval and production. The term memory disorder is intended to include dementia, slow learning and the inability to concentrate. Common causes of a memory disorder are age, severe head trauma, brain anoxia or ischemia, alcoholic-nutritional diseases, drug intoxications and neurodegenerative diseases. For example, a memory disorder is a common feature of neurodegenerative diseases, such as Alzheimer's disease (i.e. Alzheimer-type dementia). Memory disorders also occur with other kinds of dementia such as AIDS Dementia; Wernicke-Korsakoffs related dementia (alcohol induced dementia); age related dementia, multi-infarct dementia, a senile dementia caused by cerebrovascular deficiency, and the Lewy-body variant of Alzheimer's disease with or without association with Parkinson's disease. Loss of memory is also a common feature of brain-damaged patients. Non-limiting examples of causes of brain damage which may result in a memory disorder include stroke, seizure, an anaesthetic accident, ischemia, anoxia, hypoxia, cerebral edema, arteriosclerosis, hematoma or epilepsy; spinal cord cell loss; and peripheral neuropathy, head trauma, hypoglycemia, carbon monoxide poisoning, lithium intoxication, vitamin (B1, thiamine and B12) deficiency, or excessive alcohol use.

A. Delivery Methods

Various delivery systems are known and are used to administer a therapeutic of the invention, e.g., encapsulation in liposomes, microparticles, microcapsules, expression by recombinant cells, receptor-mediated endocytosis (see, e.g., Wu & Wu, *J. Biol. Chem.* 265:4429-4432, 1987), construction of a therapeutic nucleic acid as part of a retroviral or other vector, etc. Methods of introduction include, but are not limited to, intradermal, intramuscular, intraperitoneal, intravenous, subcutaneous, intranasal, and oral routes. The compounds are administered by any convenient route, for example by infusion or bolus injection, by absorption through epithelial or mucocutaneous linings (e.g., oral mucosa, rectal, and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers.

In an embodiment where the therapeutic is a nucleic acid encoding an A-chain peptide or analog therapeutic the nucleic acid is administered in vivo to promote expression of its encoded A-chain peptide by constructing it as part of an appropriate nucleic acid expression vector and administering it so that it becomes intracellular, e.g., by use of retroviral vector (see U.S. Pat. No. 4,980,286), or by direct injection, or by use of microparticle bombardment (e.g., a gene gun; Biolistic, Dupont) or coating with lipids or cell-surface receptors or transfecting agents, or by administering it in linkage to a homeobox-like peptide that is known to enter the nucleus (see e.g., Joliot et al., *Proc. Natl. Acad. Sci., U.S.A.* 88:1864-1868, 1991), etc., supra. Alternatively, a nucleic acid therapeutic can be introduced intracellularly and incorporated within host cell DNA for expression by homologous recombination.

Other methods for improving the delivery and administration of the pharmacological agent of the present invention include means for improving the ability of the pharmacological agent to cross membranes, and in particular, to cross the blood-brain barrier. One skilled in the art can readily assay the ability of an active analog, derivative, fragment or mimetic of A-chain to cross the blood-brain barrier in vivo, for example using a model of the blood-brain barrier based on a brain microvessel endothelial cell culture system, for example as described in Bowman et al., *Ann. Neurol.* 14:396-402 (1983) or Takahura et al., *Adv. Pharmacol.* 22:137-165 (1992), each of which is incorporated herein by reference. In one embodiment, the pharmacological agent can be modified to improve its ability to cross the blood-brain barrier, and in an alternative embodiment, the pharmacological agent can be co-administered with an additional agent, such as for example, an antifungal compound, that improves the ability of the pharmacological agent to cross the blood-brain barrier (see Pardridge, W. M. Neuron 2002, 36: 555-558). Alternatively, precise delivery of the pharmacological agent into specific sites of the brain, can be conducted using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images are used to determine a target site and trajectory for pharmacological agent microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The pharmacological agent can be delivered to regions, such as the cells of the spinal cord, brainstem, or brain that are associated with the disease or disorder. For example, target regions can include the medulla, pons, and midbrain, cerebellum, diencephalon (e.g., thalamus, hypothalamus), telencephalon (e.g., corpus stratium, cerebral cortex, or within the cortex, the occipital, temporal, parietal or frontal lobes), or combinations, thereof.

In a preferred embodiment, the intranasal route of administration can be used. Improved intranasal delivery methods of peptide hormones such as insulin, glucagon, growth hormone releasing hormone and others are being developed (Pontiroli, A. E. *Advanced Drug Delivery Reviews* 1998, 29: 81-87). Two recent studies have positively evaluated the use of intranasally administered insulin in treating Type 1 and Type 2 diabetes (Skyler, J. S. et al. *Lancet* 2001, 357: 331-335; Cefalu, W. T. et al. *Annals of Internal Medicine* 2001, 134: 203-207). While high doses of insulin are needed to alter peripheral glucose levels, much lower doses of A-chain or analogs are needed to ameliorate neurological disorders or enhance learning and memory as illustrated in the present invention.

In one embodiment, the pharmaceutical composition consists of 5% (2,6-DI—O-Methyl)β-cyclodextrin with A-chain or analogs. Cyclodextrins as vehicles for the promotion of insulin and other peptides across the olfactory epithelium have been extensively researched (Merkus et al. *Pharmacological Research* 1991, 8: 588-592; Shao et al. *Pharmacological Research* 1992, 9: 1157-1163; Shao et al. *Pharmacological Research* 1994, 11: 1174-1179; Schipper et al. *Calcified Tissue International* 1995, 56: 280-282; Schipper et al. *British Journal of Pharmacology* 1993, 110: 1335-1340) are safe (Marttin et al. *Journal Drug Target* 1998, 6: 17-36) and have been tested in human subjects (Pontiroli, A. E. *Advanced Drug Delivery Reviews* 1998, 29: 81-87).

B. Monitoring Treatment

Regeneration of neurons and hence treatment of disease may also be monitored by measuring specific neurotransmitters known to be altered the diseased state. For example dopamine levels can be monitored using known methods following administration of A-chain and/or analogs. To measure dopamine content, a labeled tracer is administered to the subject. The detection of the label is indicative of dopamine activity. Preferably, the labeled tracer is one that can be viewed in vivo in the brain of a whole animal, for example, by positron emission tomograph (PET) scanning or other CNS imaging techniques. See, for example, U.S. Pat. No. 6,309,634 for methods of measuring dopamine content in vivo. By treatment of disease, as used herein, is meant the reduction or elimination of symptoms of the disease of interest, as well as the regeneration of neurons. Thus, dopamine levels prior and subsequent to treatment can be compared as a measure of neuron regeneration.

Alternatively, visual symptoms of disease can be used as a measure of treatment. For example, memory tests can be monitored for improvement following treatment. Two commonly used tests to monitor dementia are the Wechsler Adult Intelligence Scale and the Cambridge Cognitive Test (CAMCOG). These tests have a number of different sections and test a variety of things, including the ability to learn new things and the ability to comprehend arithmetic and vocabulary.

C. Pharmaceutical Compositions

The pharmaceutical compositions of the invention can be prepared in various manners well known in the pharmaceutical art. The carrier or excipient may be a solid, semisolid, or liquid material that can serve as a vehicle or medium for the active ingredient. Suitable carriers or excipients are well known in the art and include, but are not limited to saline, buffered saline, dextrose, water, glycerol, ethanol, and combinations thereof. The pharmaceutical compositions may be adapted for oral, inhalation, parenteral, or topical use and may be administered to the patient in the form of tablets, capsules, aerosols, inhalants, suppositories, solutions, suspensions, powders, syrups, and the like. As used herein, the term "pharmaceutical carrier" may encompass one or more excipients. In preparing formulations of the compounds of the invention, care should be taken to ensure bioavailability of an effective amount of the agent. Suitable pharmaceutical carriers and formulation techniques are found in standard texts, such as *Remington's Pharmaceutical Sciences*, Mack Publishing Co., Easton, Pa.

Compositions will comprise sufficient genetic material to produce a therapeutically effective amount of A-chain peptide or analog, i.e., an amount sufficient to reduce or ameliorate symptoms of the disease state in question or an amount sufficient to confer the desired benefit. The compositions can contain a pharmaceutically acceptable carrier. Such carriers include any pharmaceutical agent that does not itself induce the production of antibodies harmful to the individual receiving the composition, and which may be administered without undue toxicity. Pharmaceutically acceptable carriers include, but are not limited to, cyclodextrin, (2,6-DI—O-methyl)β-cyclodextrin, sorbitol, any of the various TWEEN compounds, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable carriers and excipients is available in Remington's Pharmaceutical Sciences (Mack Pub. Co., N.J. 1991).

For oral administration, the compounds can be formulated into solid or liquid preparations, with or without inert diluents or edible carrier(s), such as capsules, pills, tablets, troches, powders, solutions, suspensions or emulsions. The tablets, pills, capsules, troches and the like also may contain one or more of the following adjuvants: binders such as microcrystalline cellulose, gum tragacanth or gelatin; excipients such as starch or lactose; disintegrating agents such as alsinic acid, Primogel™, corn starch and the like; lubricants such as stearic acid, magnesium stearate or Sterotex™; glidants such as colloidal silicon dioxide; sweetening agents such as sucrose or saccharin; and flavoring agents such as peppermint, methyl salicylate or fruit flavoring. When the dosage unit form is a capsule, it also may contain a liquid carrier such as polyethylene glycol or fatty oil. Materials used should be pharmaceutically pure and non-toxic in the amounts use. These preparations should contain at least 0.05% by weight of the therapeutic agent, but may be varied depending upon the particular form and may conveniently be between 0.05% to about 90% of the weight of the unit. The amount of the therapeutic agent present in compositions is such that a unit dosage form suitable for administration will be obtained.

For the purpose of parenteral administration, the therapeutic agent may be incorporated into a solution or suspension. These preparation should contain at least 0.1% of the active ingredient, but may be varied to be between 0.1% and about 50% of the weight thereof. The amount of the active ingredient present in such compositions is such that a suitable dosage will be obtained.

The solutions or suspensions also may include one or more of the following adjuvants depending on the solubility and other properties of the therapeutic agent: sterile diluents such as water for injections, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates; and agents for the adjustment of toxicity such as sodium chloride or dextrose. The parenteral preparation can be enclosed in ampules, disposable syringes or multiple dose vials made of glass or plastic.

The compounds can be administered in the form of a cutaneous patch, a depot injection, or implant preparation, which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones. Further information on suitable pharmaceutical carriers and formulation techniques are found in standard texts such as *Remington 's Pharmaceutical Sciences.*

The exact amount of a therapeutic of the invention that will be effective in the treatment of a particular disease or disorder will depend on a number of factors that can be readily determined by the attending diagnostician, as one of ordinarily skilled in the art, by the use of conventional techniques and by observing results obtained under analogous circumstances. Factors significant in determining the dose include: the dose; the species, subject's size, age and general health; the specific disease involved, the degree of or involvement of the severity of the disease; the response of the individual patient; the particular compound administered; the mode of administration; the bioavailability characteristics of the preparation administered; the dose regimen selected; the use of concomitant medication; and other relevant circumstances specific to the subject. Effective doses optionally may be extrapolated from dose-response curves derived from in vitro or animal model test systems. In general terms, an effective amount of a peptide of the instant invention to be administered systemically on a daily basis is about 0.1 μg/kg to about 1000 μg/kg; more preferably the daily dose is between about 1 Ag/kg to about 100 μg/kg; most preferably the daily dose is between about 5 μg/kg to about 15 μg/kg.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

The preferred form depends on the intended mode of administration and therapeutic application. The preferred mode of administration is parenteral (e.g., intravenous, subcutaneous, intraperitoneal, intramuscular, intranasal). In a preferred embodiment, the pharmacological agent is administered by intranasally.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., the pharmacological agent) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The A-chain peptide or analog of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. (See, e.g., *Sustained and Controlled Release Drug Delivery Systems*, J. R. Robinson, ed., Marcel Dekker, Inc., New York, 1978; U.S. Pat. No. 6,333,051 to Kabanov et al., and U.S. Pat. No. 6,387,406 to Kabanov et al.)

In certain embodiments, A-chain peptide or analogs of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In certain embodiments, an A-chain peptide or analogs of the present invention can be administered in a liquid form. The pharmacological agent of the present invention is freely soluble in a variety of solvents, such as for example, methanol, ethanol, and isopropanol. The pharmacological agent is, however, highly lipophilic and, therefore, substantially insoluble in water. A variety of methods are known in the art to improve the solubility of the pharmacological agent in water and other aqueous solutions. For example, U.S. Pat. No. 6,008,192 to Al-Razzak et al. teaches a hydrophilic binary system comprising a hydrophilic phase and a surfactant, or mixture of surfactants, for improving the administration of lipophilic compounds such as the pharmacological agent of the present invention.

Supplementary active compounds can also be incorporated into the compositions. In certain embodiments, an A-chain peptide or analog of the invention is coformulated with and/or coadministered with one or more additional therapeutic agents that are useful for improving the pharmacokinetics of the pharmacological agent. A variety of methods are known in the art to improve the pharmacokinetics of the pharmacological agent of the present invention. For example, U.S. Pat. No. 6,037,157 to Norbeck et al. discloses a method for improving the pharmacokinetics of the pharmacological agent by coadministration of the pharmacological agent and a drug that is metabolized by the cytochrome P450 monooxygenase, such as for example, the P450 3A4 isozyme.

Other methods of improving the pharmacokinetics of the A-chain peptides or analogs have been disclosed, for example, in U.S. Pat. No. 6,342,250 to Masters, U.S. Pat. No. 6,333,051 to Kabanov et al., U.S. Pat. No. 6,395,300 to Straub et al., U.S. Pat. No. 6,387,406 to Kabanov et al., and U.S. Pat. No. 6,299,900 to Reed et al. Masters discloses a drug delivery device and method for the controlled release of pharmacologically active agents. The drug delivery device disclosed by Masters is a film comprising one or more biodegradable polymeric materials, one or more biocompatible solvents, and one or more pharmacologically active agents dispersed uniformed throughout the film. In U.S. Pat. No. 6,333,051, Kabanov et al. disclose a copolymer networking having at least one cross-linked polyamine polymer fragment, at least one nonionic water-soluble polymer fragment, and at least one suitable biological agent, including the pharmacological agent of the present invention. According to the teachings of this patent, this network, referred to as a nanogel network, improves the therapeutic effect of the pharmacological agent by decreasing side effects and increasing therapeutic action. In another patent, U.S. Pat. No. 6,387,406, Kabanov et al. also disclose another composition for improving the oral delivery of numerous pharmacological agents. This delivery vehicle comprises a biological agent and a poly(oxyehtylene)poly (oxypropylene) block copolymer. Straub et al. disclose porous drug matrices for use with drugs, and in particular, for use with low-aqueous solubility drugs, for enhancing solubility of the drug in an aqueous solution. Reed et al. disclose a drug delivery system, which uses a dermal penetration enhancer to transport a variety of physiologically active agents across a dermal surface or mucosal membrane of a subject.

A-chain peptides or analogs of the present invention can be used alone or in combination to treat neurodegenerative disorders to produce a synergistic effect. Likewise, the pharmacological agent can be used alone or in combination with an additional agent, e.g., an agent which imparts a beneficial attribute to the therapeutic composition, e.g., an agent which effects the viscosity of the composition. The combination can also include more than one additional agent, e.g., two or three additional agents if the combination is such that the formed composition can perform its intended function.

The pharmaceutical compositions of the invention may include a "therapeutically effective amount" or a "prophylactically effective amount" of a pharmacological agent of the invention. A "therapeutically effective amount" refers to an amount effective, at dosages and for periods of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an A-chain peptide of the invention is between 0.1 µg/kg to 1,000 µg/kg body weight, administered twice per day. Preferably, administration of a therapeutically effective amount of A-chain peptide results in a concentration of pharmacological agent in the bloodstream that is between about 0.1 µM and 1000 µM. More preferably, the concentration of pharmacological agent in the blood is between about 0.1-100 µM. More preferably, the concentration of pharmacological agent in the blood is between about 0.1-10 µM. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

EXAMPLES

The following examples illustrate that the methods and compositions of the present invention can be employed to ameliorate neurological disorders, enhance cognition, learning and memory, and modulate memory disorders. The invention is demonstrated in the following examples. The following examples are merely illustrative of the present invention and should not be construed so as to limit the scope of this invention.

Example 1

Materials and Methods (i) Materials

Male Sprague Dawley rats (~300 gm) housed under controlled lighting and ad libituin food were used for all studies. All mice were tested at 8 weeks of age. Insulin, insulin A-chain, and insulin B-chain were obtained from Sigma (St. Louis, MO). Unless otherwise indicated insulin A-chain (Sigma 1-1633) oxidized ammonium salt from bovine pancreas (Gly-Ile-Val-Glu-Gln-Cys (SO3 H)-Cys(SO3 H)-Ala-Ser-Val-Cys(SO3H)-Ser-Leu-Tyr-Gln-Leu-Glu-Asn-Tyr-Cys(503H)-Asn) (SEQ ID NO:5), insulin B-chain oxidized from bovine pancreas (Phe-Val-Asn-Gln-His-Leu-Cys (SO3H)-Gly-Ser-His-Leu-Val-Glu-Ala-Leu-Tyr-Leu-Val-Cys (S03 H) -Gly-Glu-Arg-Gly-Phe-Phe-Tyr-Thr-Pro-Lys-Ala) (SEQ ID NO :6), and insulin from bovine pancreas ($C_{254}H_{377}N_{65}O_{75}S_6$) were used (SEQ ID NO:7 & SEQ ID NO:8).

(ii) Intranasal Administration of Insulin or Insulin Associated Peptides to Rats Insulin, insulin A-chain or B-chain was diluted in saline with 5-10% (2,6-DI—O-Methyl) β-cyclodextrin. Various doses of insulin, insulin A-chain or B-chain were then administered to the nasal cavity of anesthetized rats with pipette tips.

(iii) Passive Avoidance Studies

Passive avoidance was performed in an apparatus (MED Associates Inc., St. Albans, Vt.) consisting of one dark chamber and one light chamber that can be divided by a guillotine door. The training procedure was executed as previously described (N. Venable et al. *Psychopharmacology* 100, 215 (1990)). Rats were administered a 1.0 mA shock for 3 sec, mice a 0.5 mA shock for 5 sec. Retention tests were performed either at 1, 3 or 7 days post-pairing. Maximum latency was 600 sec for rats, 300 sec for mice. When pairing, if a rat or mouse did not enter the dark chamber within 2 min, the animal was excluded from the study.

In the one-trial passive avoidance procedure rats were anesthetized with isofluorane and then administered various doses of insulin, or A-chain, or B-chain intra-nasally. After a 20 minute pretreatment time, rats were placed in the light side of a two-chambered light/dark Plexiglas passive avoidance apparatus (MED Associates). Once the rat entered the dark chamber, a guillotine door was closed and a 1.0 mA shock (3 sec) was administered. The door was then raised and the rat was allowed to re-enter the light side. Latency (max 600 sec) to enter the dark chamber was taken as a measurement of associative learning. As a control, pre-training (PRE) latency times were also compared to post-training (POST) latency times illustrating that training increases latency times for all groups.

(iv) Morris Water Maze (MWM) Assessing Spatial Learning

Spatial learning was assessed using the Morris Water Maze (Morris et al. *Nature,* 1982, 297: 681). Information was relayed via a tracker (HSV Image, Hampton, UK) to a personal computer, which was quantified by a specialized computer program (Water 2020, Hampton, UK). The acquisition study was performed as described previously. Animals were anaesthetized with isofluorane then administered peptide intra-nasally 20 min before testing. Rats were given four training trials. 48 h after training, a retention test was performed: rats were allowed to find the hidden platform for one trial. Mice initially had six trials without treatment to habituate them to the procedure. The following day, they were administered vehicle or various doses of insulin, insulin A-chain or B-chain to the nasal cavity and trained for an additional four trials with the platform in a new location. For a retention test, mice were given one trial to locate the platform the next day. Latency to find the platform was considered a measure of retention of spatial learning.

(v) Elevated Plus Maze

The elevated plus maze consists of two open and two closed arms; time spent and the number of entries into open arms are indicators of neophobic anxiety in rats. The number of entries and total time spent in the open arms were tabulated over 5 min by an observer blind to the experimental condition. Animals falling off the apparatus were eliminated from the study. The peptides were infused in a total volume of 2 µl (1 µl min-1) 25 min before training with two trials per day for 5 days. The visual platform test was conducted after the last training trial on day 5 in a different location of the pool.

Example 2

Memory Enhancing Effects of Intranasal Insulin

Figure 2:
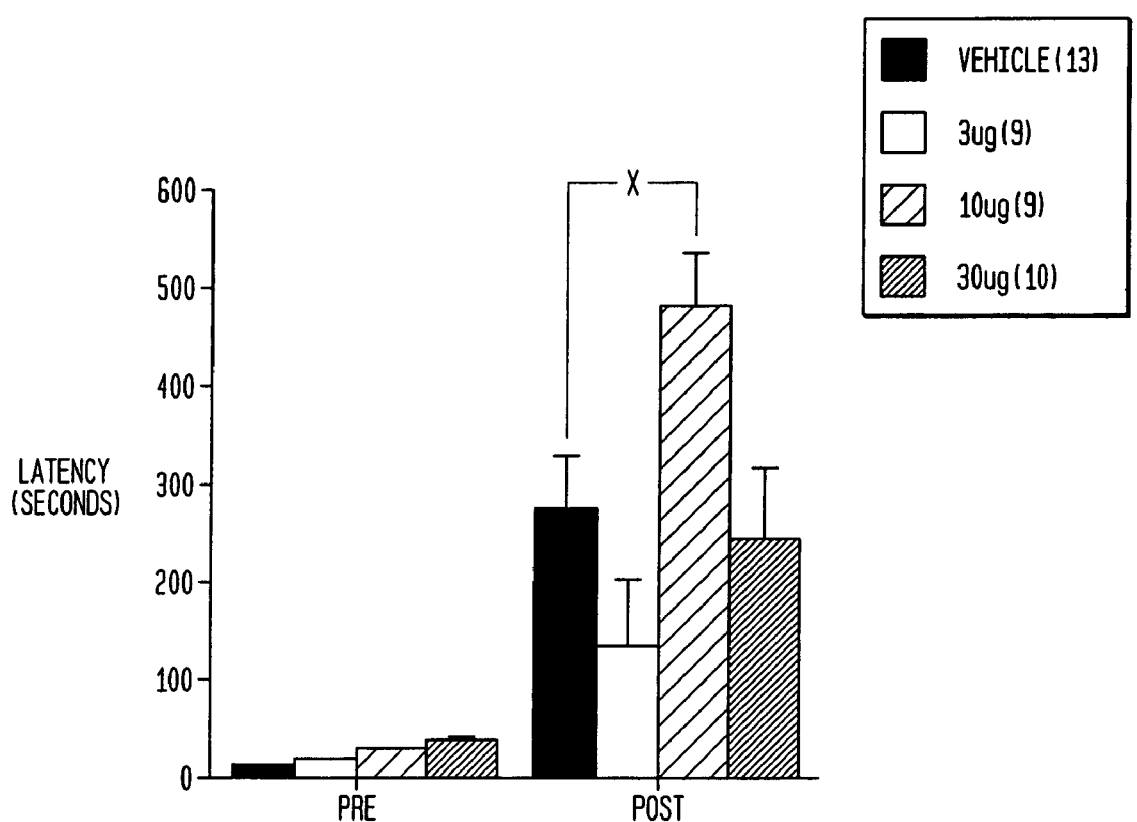

FIG. 2 shows that intranasal insulin enhances associative learning in rats. Rats were anesthetized with isofluorane and then administered (intra-nasally) various doses of insulin (pretreatment time: 20 min). Rats were then placed in the light side of a two-chambered light/dark chamber, a guillotine door was closed and a 1.0 mA shock (3 sec) was administered. The door was then raised and the rat was allowed to re-enter the light side. Latency (max 600 sec) to enter the dark chamber was taken as a measurement of associative learning. Pretreatment with intra-nasal (3-30 μg, 28 USP units/mg) significantly ($P<0.05$) enhanced latency at the 10 μg does compared to vehicle (5% (2,6-DI—O-methyl)β-cyclodextrin) alone.

As shown in FIG. 2, intranasal insulin enhanced associative learning (at the 10μg dose) as measured by the passive avoidance behavioral paradigm. These results replicate a previous study that used the invasive intracerebroventricular (ICV) route of administration with exception that insulin was given intra-nasally;

The effects of intranasal insulin on a spatial memory task was then determined by Morris Water Maze (MWM), the standard test used to measure this type of learning and memory. As shown in FIG. 3B, insulin (3 μg) significantly deceased latency to find a hidden platform when tested 48 hours after an initial training. FIG. 3B is a graph of retention tests showing a significant main effect with dose as the factor (One-Way ANOVA; F-3.068(3,37);P=0.04). Further analysis with Dunnett's test showed significant lower latency at the 3 μg does of insulin ($P<0.05*$) compared to vehicle alone.

FIG. 3A is a graph of mean (±S.E.M.) latency of acquisition times of rats to find a submerged platform in the Morris Water Maze Paradigm following administration of insulin and training. Rats were administered insulin (3-30 μg, 28 USP units/mg) or vehicle (5% (2,6-DI—O-methyl)β-cyclodextrin) intranasally and trained for four trials. Rats were then tested 48 hours following training. No significant differences occurred in acquisition between groups during training (FIG. 3A).

Example 3

Intranasal Insulin, A-Chain, and B-Chain Do Not Affect Blood Glucose Levels

Figure 4:
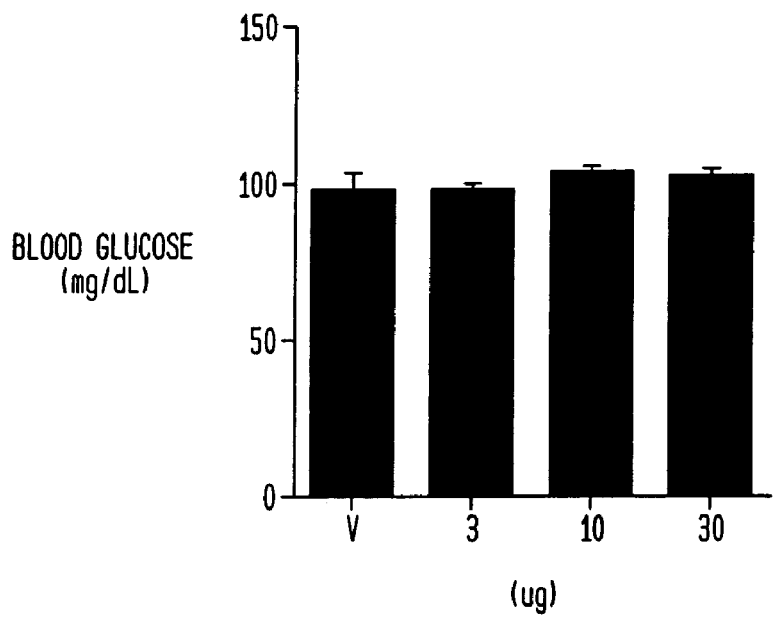

In order to test the effects on blood glucose, rats were administered various doses of insulin, or A-chain, or B-chain intra-nasally, sacrificed, and then analyzed for blood glucose levels using a glucometer (Elite XL, Bayer).The doses of insulin and insulin A-chain that enhanced learning and memory did not have any effect on peripheral blood glucose (FIG. 4), which indicated that intranasal insulin produces potent memory enhancing effects. Rats (N-5/group) were first anesthetized with isoflorane anesthesia and then administered vehicle (5% (2,6-DI—O-methyl)β-cyclodextrin) or insulin (3-30 μg, 28 USP units/mg) intra-nasally. Twenty minutes later, rats were sacrificed and blood glucose levels rapidly determined with a glucometer (Elite XL, Bayer). There were no significant differences between treatment groups as shown in FIG. 4.

Example 4

Intranasal A-Chain, but Not B-Chain Enhances Memory

Effects of insulin A- and B-chain on learning and memory also were tested using both the passive avoidance procedure and the Morris Water Maze (MWM), which measures acquisition and retention times.

Figure 5:
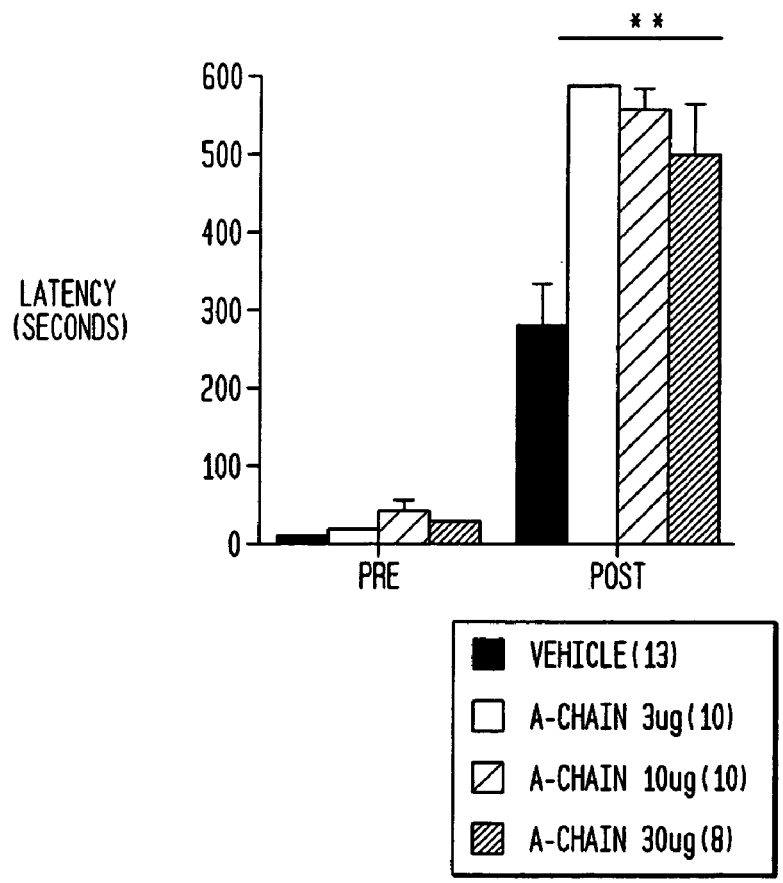

Rats were anesthetized with isofluorane then administered (intra-nasally) various doses of A-chain (pretreatment time; 20 min). Mean (±S.E.M.) latencies were measured using a one-trial passive avoidance procedure. Pretreatment with intra-nasal A-chain (3-30 μg significantly **(F=10.005(3, 37);P<0.001) enhanced latency at all doses tested compared to vehicle alone as shown in FIG. 5. In addition, mean (±S.E.M.) latencies to find a submerged platform in the Morris Water Maze Paradigm were compared. Rats were administered A-chain (3-30 μg) or vehicle (5% 2.6-DI-Omthyl)p-cyclodextrin) intra-nasally and trained for four trials. The rats were then tested 48 hours following training. No significant differences occurred in acquisition between groups during training (FIG. 6A). However, analysis of retention tests 48 hours following training (FIG. 6B) yielded a significant main effect (F-3.551(3,39);P-0.023) indicating that intra-nasal A-chain enhances spatial memory. Further analysis with Dunnett's test showed significant lower latency following administration of A-chain at the 3 μg and 10 μg doses ($P<0.05*$) compared to vehicle alone.

Figure 7:
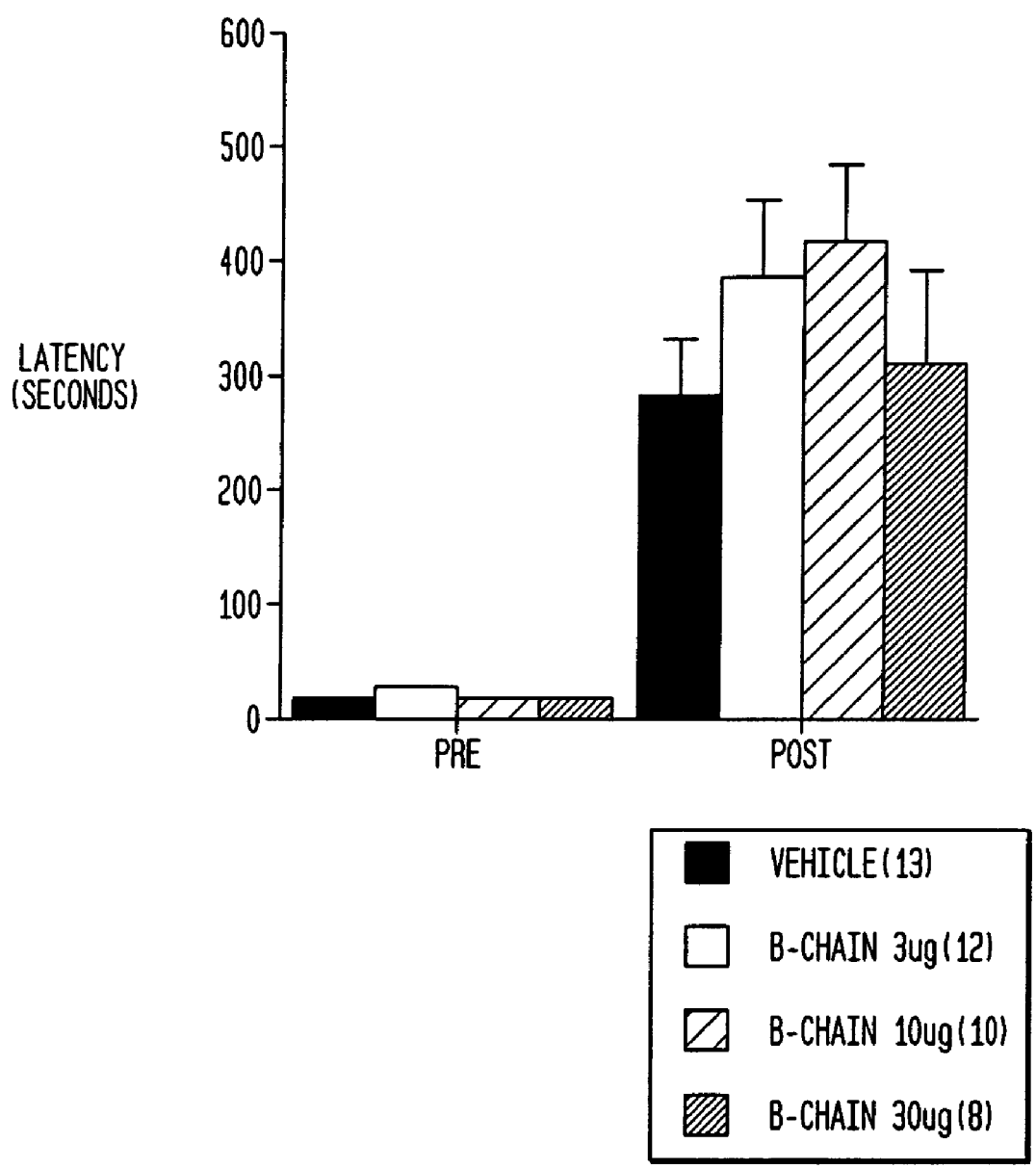
Figure 8B:
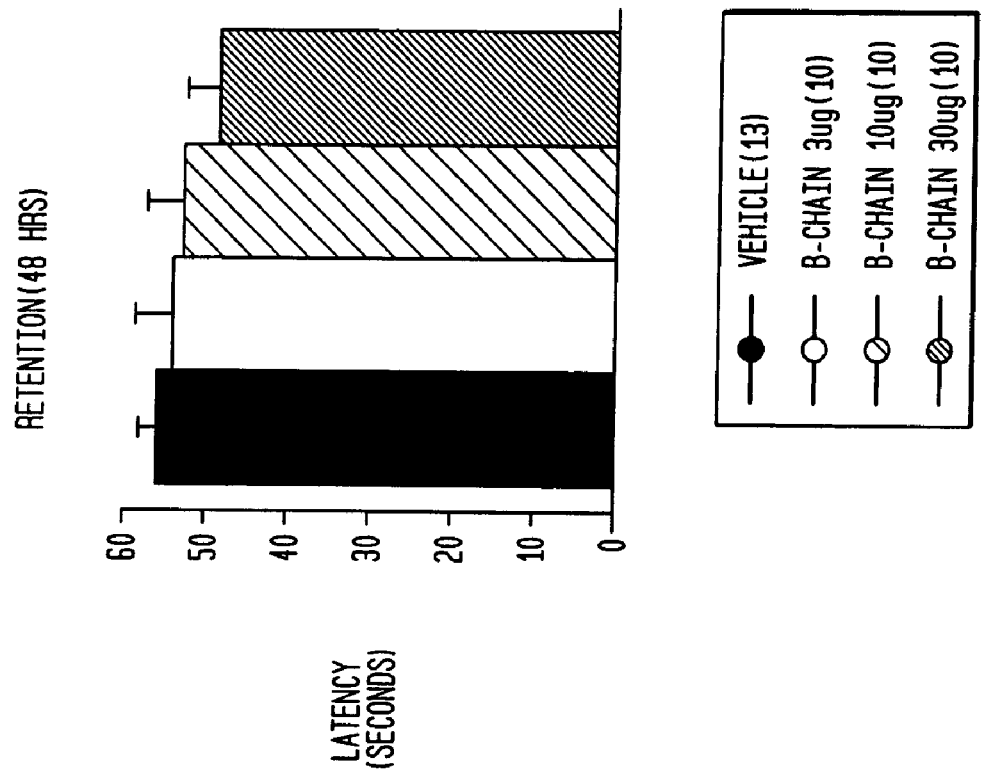
Figure 8A:
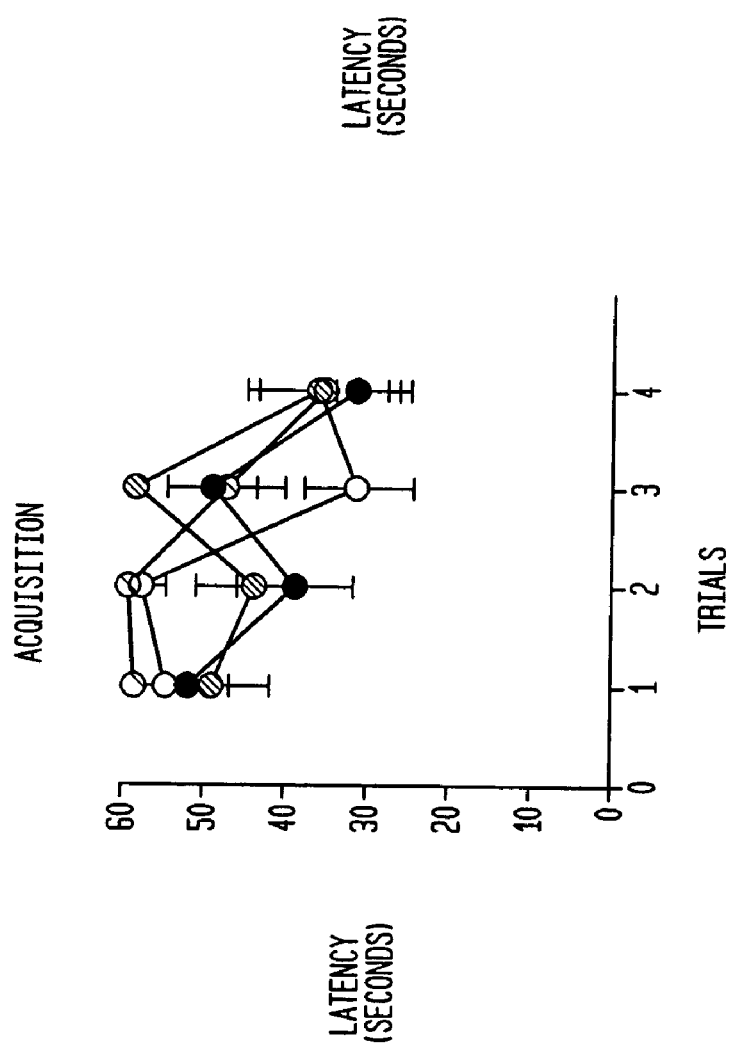
Figure 9:
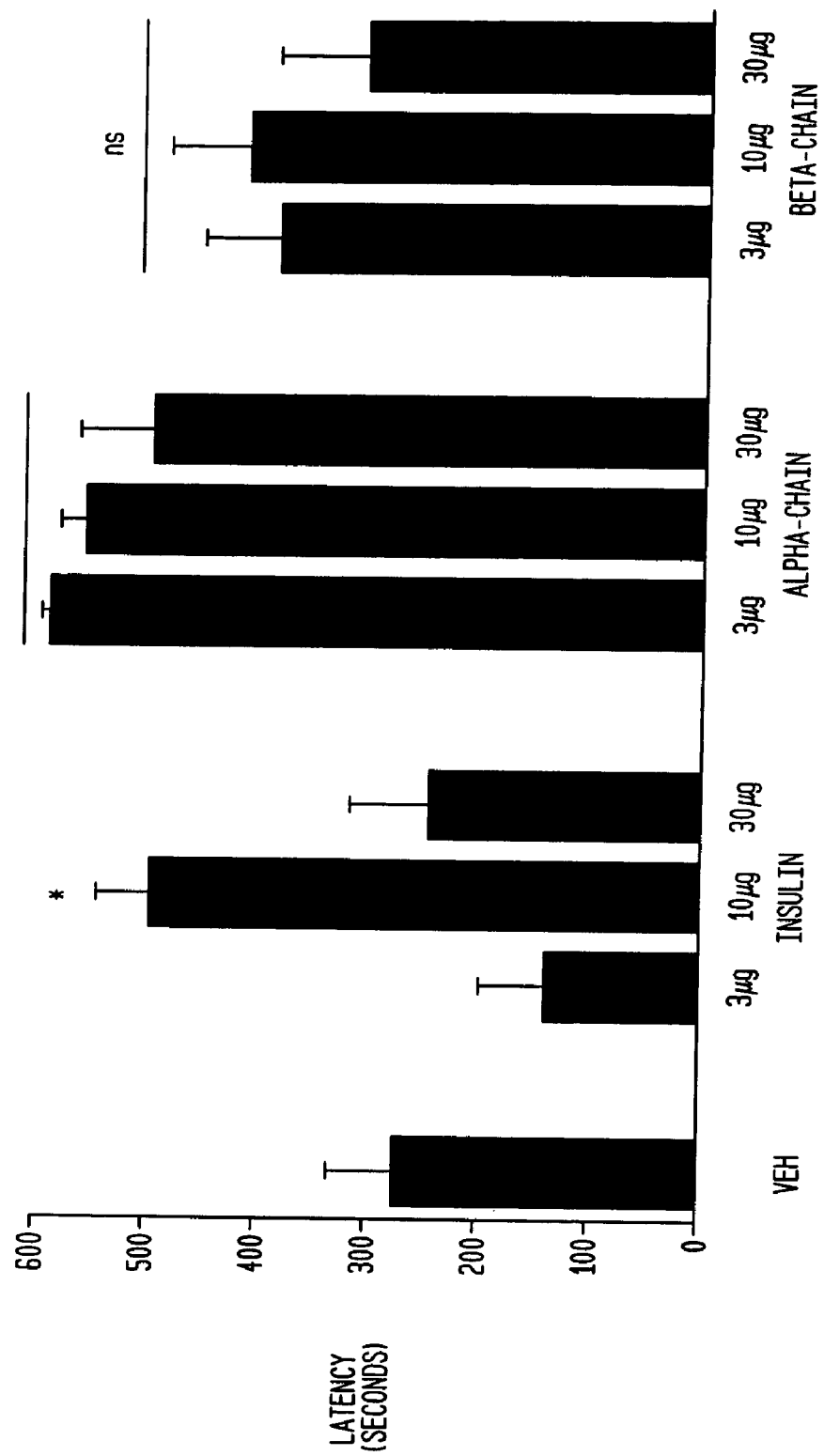
FIG. 9 is a bar graph showing that insulin and A-chain, but not B-Chain, enhance retention of associative learning (24 hrs)

Insulin B-chain was also tested in both passive avoidance and MWM behavioral tests. Mean (±S.E.M.) latencies were measured using a one-trial passive avoidance procedure for rats that were anesthetized with isofluorane then administered (intranasally) various doses of B-chain. Pretreatment with intra-nasal B-chain (3-30 μg did not significantly (F=0.906 (3,39);P=0.447) enhance latency times at any dose tested (FIG. 7). Mean (±S.E.M.) latencies to find a submerged platform in the Morris Water Maze Paradigm were measured for rats that were administered B-chain (3-30 μg) or vehicle (5%(2,6-DI-Omthyl)β-cyclodextrin) intra-nasally and trained for four trials. Rats were then tested 48 hours following training. No significant differences occurred in acquisitions between the groups during training (FIG. 8A) or retention tests (FIG. 8B) at doses tested (F=0.702(3,38);P=0.557). FIG. 9 shows that insulin and A-chain, but not B-chain enhances retention of associative learning (24 hours).

A-chain showed potent memory enhancing effects in both passive avoidance (FIG. 5) and MWM (FIG. 6) behavioral paradigms. In contrast, B-chain did not enhance learning and memory in either paradigm (FIG. 7 and FIG. 8).

Example 5

A-Chain Increases Passive Avoidance Response

In order to study the effects of insulin A-chain on the passive avoidance response, rats were pretreated intranasally with one of three dose levels (3 μg, 10 μg, or 30 μg) of A-chain in 5% β cyclodextrin. A control group received vehicle (5% cyclodextrin) alone. With three dose levels for each of the peptides studied, a total of seven (4) groups were employed, each group having 8-13 rats, for a total of 41 rats tested. On the first day of conditioning, the pretreated rats were administered a single foot shock trial (0.1 mA over 3 seconds) after entering the dark compartment. The animals were replaced in the test apparatus and latencies again were measured on Days 1, 3, and 7 following the aversive stimulus.

Figure 10:
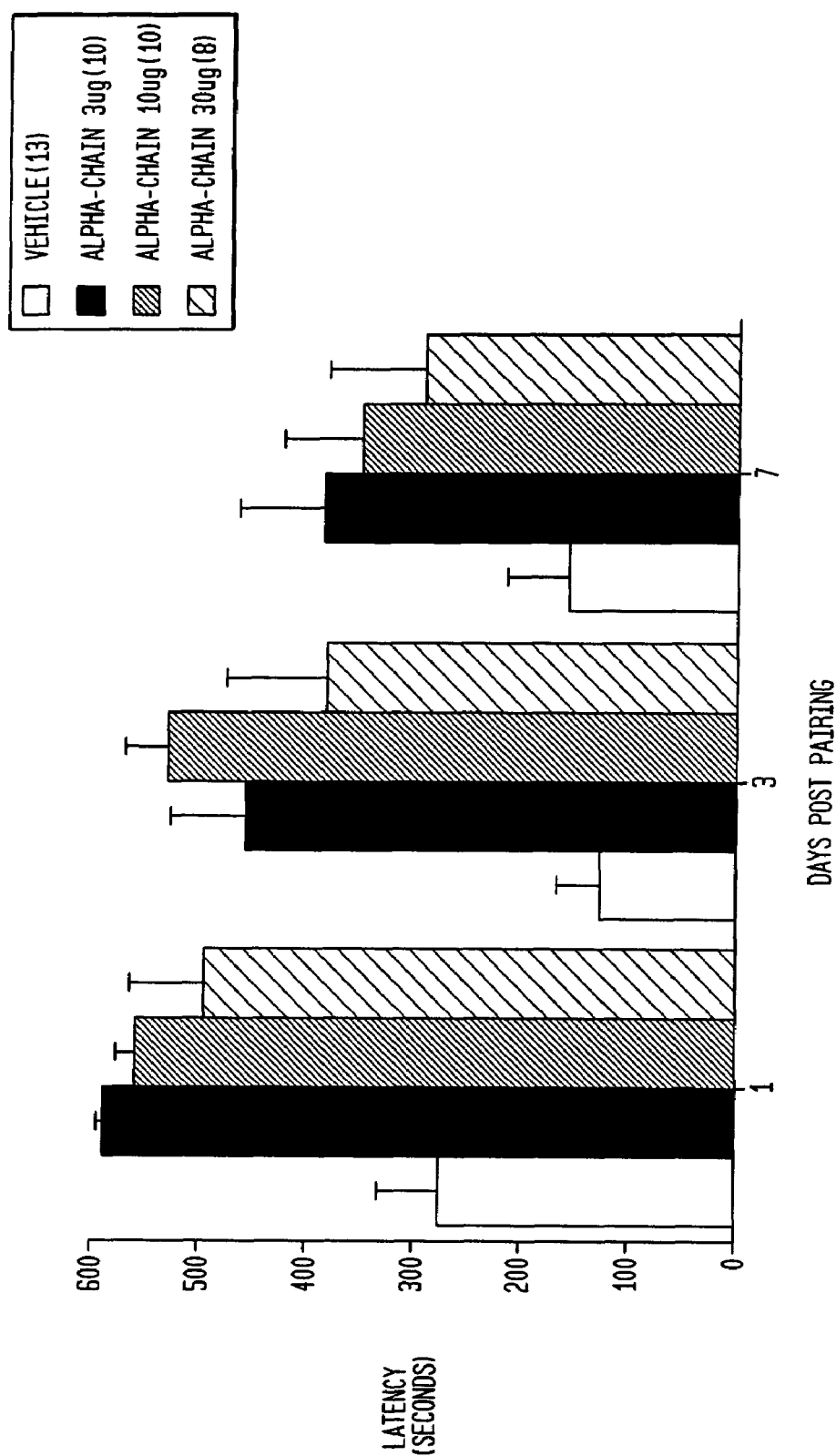
FIG. 10 is a bar graph showing that intra-nasal insulin A-chain (3-30 µg) enhances associative learning compared to control (vehicle only) as evidenced by the increase in latency in passive avoidance studies.

As predicted, the control animals (N=13) showed short latencies to enter the dark room prior to exposure to the single mild shock. Similarly, all other groups had increased latencies (FIG. 10). At 24 hours (Day 1) following the initial test, and delivery of the single shock, the animals were replaced in the test apparatus and latency again measured. Those control rats, which had learned that the aversive stimulation was associated with entering the dark room, had mean latencies of less than 300 seconds. All groups that had been administered A-chain had increased latencies, greater than 475 seconds.

On Day 3, rats were again tested in the apparatus. By this time the control rats had started to forget the aversive stimulus; thus, their latencies decreased to less than 150 seconds see FIG. 10. All other groups had only a slight drop in latencies (See FIG. 10).

On Day 7 following delivery of the peptide, the rats were again placed in the test apparatus. The rats administered A-chain still had mean latencies well significantly above that of the control group. Interestingly, rats administered 3 µg A-chain had the greatest and most prolonged increase in latency. Thus, as shown in FIG. 10, intranasal delivery of insulin A-chain enhances associative learning.

Example 6

Insulin A-Chain Interacts with a Tyrosine Kinase Coupled Receptor

The effect of the insulin antagonist α2HSG on the improved learning attributed to insulin or A-chain was explored. Rats were anesthetized with isofluorane then administered (intranasally) insulin alone (10 µg) or various doses of the insulin antagonist α2HSG (3-30 µg) in combination with insulin (10 µg). Pretreatment with insulin (10 µg) alone significantly ($P<0.05$) enhanced latency time, as tested in a one-trial passive avoidance procedure, compared to vehicle alone and pretreatment with α2HSG (3-30 µg) blocked enhancement of latency times by insulin ($F=3.700$ (4,35);$P=0.01$) (FIG. 11).

In addition, the mean (±S.E.M.) latencies using a one-trial passive avoidance procedure were measured for rats that were anesthetized with isofluorane and then administered (intranasally) A-chain alone (3 µg), the insulin antagonist a 2HSG (30 µg) alone, or a combination of both (FIG. 12). Pretreatment with A-chain (3 µg) alone significantly ($t=4.634(21)$; $P<0.01$) enhanced latency time compared to vehicle alone. Pretreatment with α2HSG (30 µg) blocked enhancement of latency times by A-chain ($t=6.345(15)$;$P<0.01$). There was no difference between antagonist alone and vehicle alone ($t=0.915(18)$;$P=0.372$).

As shown in FIGS. 11, the robust facilitation of learning and memory by insulin were blocked by the tyrosine kinase inhibitor α2HSG (3 µg), a potent inhibitor of insulin-induced tyrosine phosphorylation of Shc. These effects were mediated predominantly through the insulin receptor. High doses of α2HSG (30 µg) also were able to antagonize the A-chain effect (FIG. 12). The base peptide described herein, insulin A-chain, represents an example of a peptide that can be used to treat, either prophylactically or therapeutically, nervous system or neurological disorders associated with neuronal loss or dysfunction and facilitate learning, memory, and cognition. The scope of this invention is not limited to this example; the example is used to illustrate the technology of the present invention. Those skilled in the art are familiar with peptide synthesis techniques so that any analog, derivative, fragment, or mimetic that retains the biological activity of insulin A-chain in cellular or animal models can be used for the purposes of the present invention.

Example 7

Insulin, A-Chain, and B-Chain Do Not Affect Locomotor Activity

Since drugs that effect arousal and attention generally are psychomotor stimulants, insulin, insulin A-chain and insulin B-chain were tested in a fully automated and comprehensive locomotor activity apparatus. Rats were pretreated with either 3-30 µg/kg of insulin, A-chain, or B-chain in 5% β cyclodextrin intranasally or vehicle (5% β cyclodextrin). Following pretreatment, the rats were placed for 30 minutes in an open field testing chamber (17"×17"×12" H) where movement was detected every 50 ms by infrared photo beam emitter and detector strips at 1" and 10" from the bottom of the chamber. The activity chambers were lined to a PC computer and data was compiled via Activity Monitor Software (4.0, MED Associates, St. Albans, Vt.). The distance traveled did not differ between treatments (data not shown). Intranasal insulin, A-chain, or B-chain do not affect swimming speed compared to vehicle.

Equivalents

Those skilled in the art will appreciate, or be able to ascertain using no more than routine experimentation, further features and advantages of the invention based on the above-described embodiments. Accordingly, the invention is not to be limited by what has been particularly shown and described, except as indicated by the appended claims. All publications and references are herein expressly incorporated by reference in their entirety.

We claim:

1. A method for improving memory retention and/or memory acquisition in a subject with a neurological disorder, comprising administering to the subject with the neurological disorder an amount sufficient to improve memory retention and/or memory acquisition in the subject of a pharmaceutical composition comprising a therapeutic peptide, the therapeutic peptide consisting of purified insulin A-chain peptide.

2. A method for improving memory retention in a subject with a neurological disorder characterized by an impairment in memory retention, comprising administering to the subject with the neurological disorder an amount sufficient to improve memory retention in the subject of a pharmaceutical composition comprising a therapeutic peptide, the therapeutic peptide consisting of purified insulin A-chain peptide.

3. A method for improving memory acquisition in a subject with a neurological disorder characterized by an impairment in memory acquisition, comprising administering to the subject with the neurological disorder an amount sufficient to improve memory acquisition in the subject of a pharmaceutical composition comprising a therapeutic peptide, the therapeutic peptide consisting of purified insulin A-chain peptide.

4. The method of claim 1 wherein the therapeutic peptide has an amino acid sequence selected from the group consisting of SEQ ID NO:1, a sequence having conservative amino acid substitutions to SEQ ID NO:1, SEQ ID NO:3, and a sequence having conservative amino acid substitutions to SEQ ID NO:3.

5. The method of claim 1 wherein the pharmaceutical composition further comprises a pharmaceutically acceptable carrier.

6. The method of claim 1, wherein the administration of a therapeutically effective amount of the therapeutic peptide enhances associative learning in the subject.

7. The method of claim 1, wherein the administration of a therapeutically effective amount of the therapeutic peptide modulates activity of a tyrosine kinase coupled receptor.

8. The method of claim 5, wherein the pharmaceutically acceptable carrier is a carrier formulated for intranasal, intraperitoneal, intracerebroventricular, intradermal, intramuscular, intravenous, or subcutaneous delivery.

9. The method of claim 8, wherein the pharmaceutical composition further comprises cyclodextrin.

10. The method of claim 1 wherein the therapeutic peptide is selected from the group consisting of bovine insulin A-chain peptide, and human insulin A-chain peptide.

11. The method of claim 1 wherein the therapeutic peptide is selected from the group consisting of SEQ ID NO: 1 and SEQ ID NO: 3.

12. A method of improving memory retention and/or memory acquisition in a subject with a neurological disorder comprising administering to the subject with the neurological disorder a pharmaceutical composition comprising an amount sufficient to improve memory retention and/or memory acquisition in the subject of a therapeutic peptide, the therapeutic peptide comprising purified insulin A-chain peptide, but not insulin-B chain, such that the therapeutic peptide modulates activity of a tyrosine kinase coupled receptor.

13. The method of claim 12, wherein the pharmaceutical composition, further comprising a pharmaceutically acceptable carrier and wherein the pharmaceutically acceptable carrier is a carrier formulated for intranasal, intraperitoneal, intracerebroventricular, intradermal, intramuscular, intravenous, or subcutaneous delivery.

14. The method of claim 13 wherein the carrier is formulated for intranasal delivery.

15. The method of claim 12 wherein the therapeutic peptide consists of less than 22 amino acids.

16. The method of claim 1 wherein the amount sufficient of insulin A-chain peptide is in a range from about 0.1 µg/kg to about 1000 µg/kg.

17. The method of claim 16 wherein the amount sufficient of insulin A-chain peptide is in a range from about 5 µg/kg to about 15 µg/kg.

18. The method of claim 12 wherein the amount sufficient of insulin A-chain peptide is in a range from about 0.1 µg/kg to about 1000 µg/kg.

19. The method of claim 18 wherein the amount sufficient of insulin A-chain peptide is in a range from about 5µg/kg to about 15 µg/kg.

20. The method of claim 1 wherein the amount sufficient of insulin A-chain peptide comprising a concentration of insulin A-chain peptide in a bloodstream of the subject in a range from about 0.1 µM to about 1000 µM.

21. The method of claim 20 wherein the amount sufficient of insulin A-chain peptide comprising a concentration of insulin A-chain peptide in the bloodstream in a range from about 0.1 µM to about 10 µM.

22. The method of claim 12 wherein the amount sufficient of insulin A-chain peptide comprising a concentration of insulin A-chain peptide in a bloodstream of the subject in a range from about 0.1 µM to about 1000 µM.

23. The method of claim 22 wherein the amount sufficient of insulin A-chain peptide comprising a concentration of insulin A-chain peptide in the bloodstream in a range from about 0.1 µM to about 10 µM.

* * * * *

SEQUENCE LISTING

```
<160> NUMBER OF SEQ ID NOS: 14

<210> SEQ ID NO 1
<211> LENGTH: 21
<212> TYPE: PRT
<213> ORGANISM: Bos taurus

<400> SEQUENCE: 1

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 2
```

<211> LENGTH: 25
<212> TYPE: PRT
<213> ORGANISM: Homo sapiens

<400> SEQUENCE: 2

Arg Pro Tyr Val Ala Leu Phe Glu Lys Cys Cys Leu Ile Gly Ala Cys
1               5                   10                  15

Thr Lys Arg Ser Leu Ala Lys Tyr Cys
            20                  25

<210> SEQ ID NO 3
<211> LENGTH: 21
<212> TYPE: PRT
<213> ORGANISM: Homo sapiens

<400> SEQUENCE: 3

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 4
<211> LENGTH: 30
<212> TYPE: PRT
<213> ORGANISM: Homo sapiens

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 5
<211> LENGTH: 21
<212> TYPE: PRT
<213> ORGANISM: Bos taurus
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 5

Gly Ile Val Glu Gln Xaa Xaa Ala Ser Val Xaa Ser Leu Tyr Gln Leu
1               5                   10                  15

Glu Asn Tyr Xaa Asn
            20

<210> SEQ ID NO 6
<211> LENGTH: 30
<212> TYPE: PRT
<213> ORGANISM: Bos taurus
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid -continued

```
<400> SEQUENCE: 6

Phe Val Asn Gln His Leu Xaa Gly Ser His Leu Val Glu Ala Leu Tyr
1               5                   10                  15

Leu Val Xaa Gly Glu Arg Gly Phe Phe Tyr Thr Pro Lys Ala
            20                  25                  30

<210> SEQ ID NO 7
<211> LENGTH: 21
<212> TYPE: PRT
<213> ORGANISM: Bos taurus

<400> SEQUENCE: 7

Gly Ile Val Glu Gln Cys Cys Ala Ser Val Cys Ser Leu Tyr Gln Leu
1               5                   10                  15

Glu Asn Tyr Cys Asn
            20

<210> SEQ ID NO 8
<211> LENGTH: 30
<212> TYPE: PRT
<213> ORGANISM: Bos taurus

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala
            20                  25                  30

<210> SEQ ID NO 9
<211> LENGTH: 21
<212> TYPE: PRT
<213> ORGANISM: Sus scrofa

<400> SEQUENCE: 9

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 10
<211> LENGTH: 21
<212> TYPE: PRT
<213> ORGANISM: Mus musculus

<400> SEQUENCE: 10

Gly Ile Val Asp Gln Cys Cys Thr Ser Ile Cys Ser Leu Tyr Gln Leu
1               5                   10                  15

Glu Asn Tyr Cys Asn
            20

<210> SEQ ID NO 11
<211> LENGTH: 21
<212> TYPE: PRT
<213> ORGANISM: Ovis aries

<400> SEQUENCE: 11

Gly Ile Val Glu Gln Cys Cys Ala Gly Val Cys Ser Leu Tyr Gln Leu
1               5                   10                  15

Glu Asn Tyr Cys Asn
            20
```

```
<210> SEQ ID NO 12
<211> LENGTH: 21
<212> TYPE: PRT
<213> ORGANISM: Oryctolagus cuniculus

<400> SEQUENCE: 12

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 13
<211> LENGTH: 21
<212> TYPE: PRT
<213> ORGANISM: Cercopithecus aethiops

<400> SEQUENCE: 13

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 14
<211> LENGTH: 21
<212> TYPE: PRT
<213> ORGANISM: Canis lupus

<400> SEQUENCE: 14

Gly Ile Val Glu Gln Cys Cys Thr Ser Ile Cys Ser Leu Tyr Gln Leu
1               5                   10                  15

Glu Asn Tyr Cys Asn
            20
```